US010968464B2

(12) United States Patent
Mittal

(10) Patent No.: US 10,968,464 B2
(45) Date of Patent: Apr. 6, 2021

(54) ADENOVIRAL VECTOR SYSTEM FOR GENE DELIVERY

(71) Applicant: Purdue Research Foundation, West Lafayette, IN (US)

(72) Inventor: Suresh Kumar Mittal, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/359,973

(22) Filed: Mar. 20, 2019

(65) Prior Publication Data

US 2019/0292562 A1  Sep. 26, 2019

Related U.S. Application Data

(60) Provisional application No. 62/646,936, filed on Mar. 23, 2018.

(51) Int. Cl.
*C12N 15/00* (2006.01)
*C12N 5/00* (2006.01)
*C12N 15/86* (2006.01)
*C07K 14/09* (2006.01)
*C07K 14/11* (2006.01)

(52) U.S. Cl.
CPC .............. *C12N 15/86* (2013.01); *C07K 14/09* (2013.01); *C07K 14/11* (2013.01); *C12N 2710/10041* (2013.01)

(58) Field of Classification Search
None
See application file for complete search history.

(56) References Cited

U.S. PATENT DOCUMENTS 8,932,607 B2 * 1/2015 Custers .................... C12N 7/00
424/204.1

OTHER PUBLICATIONS

Hess et al., "The Complete Nucleotide Sequence of the Egg Drop Syndrome Virus: An Intermediate between Mastadenoviruses and Aviadenoviruses", Virology 238: 145-156 (Year: 1997).*
Zhu et al., "Isolation, identification, and complete genome sequence of a bovine adenovirus type 3 from cattle in China," Virology Journal 8:557 (Year: 2011).*
Mittal et al., "Development of a bovine adenovirus type 3-based expression vector", Journal of General Virology, 76: 93-102 (Year: 1995).*
Sharma, A., et al., "Evaluation of cross-reactive cell-mediated immune responses among human, bovine and porcine adenoviruses", Gene Therapy, 17, pp. 634-642, 2010.
Bangari, D., et al., "Development of nonhuman adenoviruses as vaccine vectors", Vaccine, 24, pp. 849-862, 2006.
Singh, N., et al., "Bovine Adenoviral Vector-based H5N1 Influenza Vaccine Overcomes Exceptionally High Levels of 'Pre-existing Immunity Against Human Adenovirus" Molecular Therapy, 16, pp. 965-971, 2008.

(Continued)

*Primary Examiner* — M Franco G Salvoza
(74) *Attorney, Agent, or Firm* — Purdue Research Foundation; Liang Zeng Yan

(57) ABSTRACT

Disclosed herein a unique cell line system to generate a novel bovine adenovirus vector that provides more gene insertion capabilities and better immunogenicity for inserted antigens. The unique cell line is used for generating and growing of the new adenovirus vectors for gene delivery or recombinant vaccine production.

5 Claims, 16 Drawing Sheets

Figure 1:
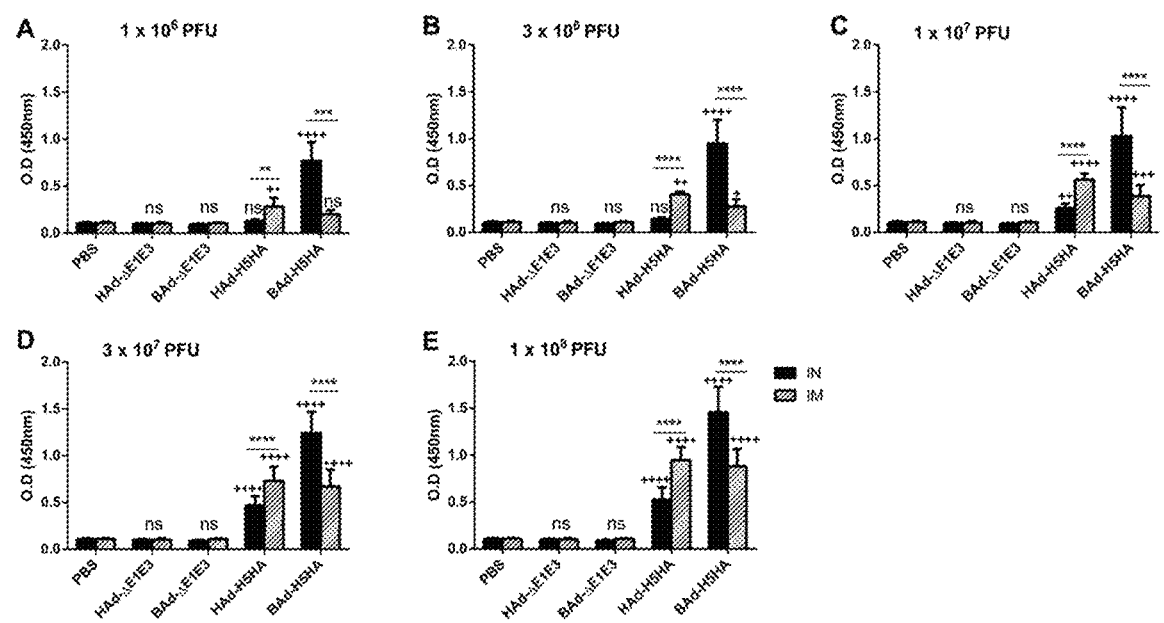

Specification includes a Sequence Listing.

(56) References Cited

OTHER PUBLICATIONS

Sharma, A., et al., "Comparative analysis of vector biodistribution, persistence and gene expression following intravenous delivery of bovine, porcine and human adenoviral vectors in a mouse model", Virology, 386, pp. 44-54.

Bangari, D., et al., "Bovine adenovirus type 3 internalization is independent of primary receptors of human adenovirus type 5 and porcine adenovirus type 3", Biochemical and Biophysical Research Communications, 331, pp. 1478-1484, 2005.

Li, X., et al., "Bovine adenovirus serotype 3 utilizes sialic acid as a cellular receptor for virus entry", Virology, 392, pp. 162-168, 2009.

Hoelscher, M., et al., "A Broadly Protective Vaccine against Globally Dispersed Clade 1 and Clade 2 H5N1 Influenza Viruses", The Journal of Infectious Diseases, 197, pp. 1185-1188, 2008.

Vemula, S., et al., "Broadly Protective Adenovirus-Based Multivalent Vaccines against Highly Pathogenic Avian Influenza Viruses for Pandemic Preparedness", PLOS One, e62496, pp. 12, 2013.

Gurwith, M., et al, "Safety and immunogenicity of an oral, replicating adenovirus serotype 4 vector vaccine for H5N1 infl uenza: a randomised, double-blind, placebo-controlled, phase 1 study" Lancet Infect Dis, 13, pp. 238-250, 2013.

Osman, M., et al., "A third generation vaccine for human visceral leishmaniasis and post kala azar dermal leishmaniasis: First-in-human trial of ChAd63-KH" PLOS Neglected Tropical Diseases, p. 24, 2017.

Hoelscher, M. et al., "Development of adenoviral-vector-based pandemic influenza vaccine against antigenically distinct human H5N1 strains in mice", Lancet, 367, pp. 475-481, 2006.

Hoelscher, M., et al., "New Pre-pandemic Influenza Vaccines: An Egg- and Adjuvant-independent Human Adenoviral Vector Strategy Induces Long-lasting Protective Immune Responses in Mice", Clinical Pharmacology and Therapeutics, 82, pp. 665-671, 2007.

Vemula, S., et al., "Beta-defensin 2 enhances immunogenicity and protection of anadenovirus-based H5N1 influenza vaccine at an early time", Virus Research, 178, pp. 398-403, 2013.

Hassan, A., et al., "Adenovirus vector-based multi-epitope vaccine provides partial protection against H5, H7, and H9 avian influenza viruses" PLOS One, pp. 15, 2017.

Van Olphen, A., et al., "Development and Characterization of Bovine Human Hybrid Cell Lines That Efficiently Support the Replication of both Wild-Type Bovine and Human Adenoviruses and Those with E1 Deleted", Journal of Virology, 76, pp. 5882-5892, 2002.

Pandey, A., et al., "Impact of Preexisting Adenovirus Vector Immunity on Immunogenicity and Protection Conferred with an Adenovirus-Based H5N1 Influenza Vaccine" Plus One, e33428, pp. 9, 2012.

Van Olphen, A., et al., "Characterization of Bovine Adenovirus Type 3 E1 Proteins and Isolation of E1-Expressing Cell Lines", Virology, 295, pp. 108-118, 2002.

* cited by examiner

```
1   MGAGQSSPAT GSQNQSGNTG SIINNYYMQQ YQNSMDTQLG DNAISGGSNE GSTDTTSTHT
61  TNTQNNDWFS KLASSAFSGLF GALLA DKKT EETTLLEDRI LTTRNGHTTS TTQSSVGVTY
121 GYATAEDFVS GPNTSGLETR VVQAERFFKT HLFDWVTSDS FGRCHLLELP TDHKGVYGSL
181 TDSYAYMRNG WDVEVTAVGN QFNGGCLLVA MVPELCSIQK RELYQLTLFP HQFINPRTNM
241 TAHITVPFVG VNRYDQYKVH KPWTLVVMVV APLTVNTEGA PQIKVYANIAPTN VHVAGEFPSKE
    GIFP VA CSDGYGGLVT TDPKTADPVY GKVFNPPRNQ LPGRFTNLLD VAEACPTFLR
361 FEGGVPYVTT KTDSDRVLAQ FDMSLAAKHM SNTFLAGLAQ YYTQYSGTIN PHFMFTGPTD
421 AKARYMIAYA PPGMEPPKTP EAAAHCIHAE WDTGLNSKFT FSIPYLSAAD YAYTASDVAE
481 TTNVQGWVCL FQITHGKADG DALVVLASAG KDFELRLPV DARAE TTSAGE SADPVTTTVE
541 NYGGETQIQR RQHTDVSFIM DRFVKVTPQN QINILDLMQI PSHTLVGALL RASTYYFSDL
601 EIAVKHEGDL TWVPNGAPEK ALDNTTNPTA YHKAPLTRLA LPYTAPHRVL ATVYNGECRY
661 SRNAVPNVRG DLQVLAQKVV RTLPTSFNYG AIKATRVTEL LYRMKRAETY CPRPLLAIHP
721 TEARHKQKIV APVKQ
```

FIG. 14

```
  1 MGAGQSSPAT GSQNQSGNTG SIINNYYMQQ YQNSMDTQLG DNAISGGSNE GSTDTTSTHT
 61 TNTQNNDWFS KLASSAFSGLF RRHRR DKKT EETTLLEDRI LTTRNGHTTS TTQSSVGVTY
121 GYATAEDFVS GPNTSGLETR VVQAERFFKT HLFDWVTSDS FGRCHLLELP TDHKGVYGSL
181 TDSYAYMRNG WDVEVTAVGN QFNGGCLLVA MVPELCSIQK RELYQLTLFP HQFINPRTNM
241 TAHITVPFVG VNRYDQYKVH KPWTLVVMVV APLTVNTEGA PQIKVYANIAPTN RRHRR GIFP
VA CSDGYGGLVT TDPKTADPVY GKVFNPPRNQ LPGRFTNLLD VAEACPTFLR
361 FEGGVPYVTT KTDSDRVLAQ FDMSLAAKHM SNTFLAGLAQ YYTQYSGTIN PHFMFTGPTD
421 AKARYMIAYA PPGMEPPKTP EAAAHCIHAE WDTGLNSKFT FSIPYLSAAD YAYTASDVAE
481 TTNVQGWVCL FQITHGKADG DALVVLASAG KDFELRLPV RRHRR  TTSAGE SADPVTTTVE
541 NYGGETQIQR RQHTDVSFIM DRFVKVTPQN QINILDLMQI PSHTLVGALL RASTYYFSDL
601 EIAVKHEGDL TWVPNGAPEK ALDNTTNPTA YHKAPLTRLA LPYTAPHRVL ATVYNGECRY
661 SRNAVPNVRG DLQVLAQKVV RTLPTSFNYG AIKATRVTEL LYRMKRAETY CPRPLLAIHP
721 TEARHKQKIV APVKQ
```

FIG. 15

SEQUENCE LISTING

```
<160> NUMBER OF SEQ ID NOS: 9

<210> SEQ ID NO 1
<211> LENGTH: 2574
<212> TYPE: DNA
<213> ORGANISM: artificial
<220> FEATURE:
<223> OTHER INFORMATION: Bovine adenovirus type 3 with E1 deletion

<400> SEQUENCE: 1
tagacagact tttttctcatt ttctcacact ccgtcgtccg cttcagagct ctgcgtcttc    60
gctgccacca tgaagtacct ggtcctcgtt ctcaacgacg gcatgagtcg aattgaaaaa   120
gctctcctgt gcagcgatgg tgaggtggat ttagagtgtc atgaggtact tccccttct   180 cccgcgcctg tccccgcttc tgtgtcaccc gtgaggagtc ctcctcctct gtctccggtg   240
tttcctccgt ctccgccagc cccgcttgtg aatccagagg cgagttcgct gctgcagcag   300
tatcggagag agctgttaga gaggagcctg ctccgaacgg ccgaaggtca gcagcgtgca   360
gtgtgtccat gtgagcggtt gcccgtggaa gaggatgagt gtctgaatgc cgtaaatttg   420
ctgtttcctg atccctggct aaatgcagct gaaaatgggg gtgatatttt taagtctccg   480
gctatgtctc cagaaccgtg gatagatttg tctagctacg atagcgatgt agaagaggtg   540
actagtcact tttttctgga ttgccctgaa gaccccagtc gggagtgttc atcttgtggg   600
tttcatcagg ctcaaagcgg aattccaggc attatgtgca gtttgtgcta catgcgccaa   660
acctaccatt gcatctatag taagtacatt ctgtaaaaga acatcttggt gatttctagg   720
tattgtttag ggattaactg ggtggagtga tcttaatccg gcataaccaa atacatgttt   780
tcacaggtcc agtttctgaa gaggaaatgt gagtcatgtt gactttggcg cgcaagagga   840
aatgtgagtc atgttgactt tggcgcgccc tacggtgact ttaaagcaat ttgaggatca   900 ctttttttgtt agtcgctata aagtagtcac ggagtcttca tggatcactt aagcgttctt   960
ttggatttga agctgcttcg ctctatcgta gcggggggctt caaatcgcac tggagtgtgg  1020
aagaggcggc tgtggctggg acgcctgact caactggtcc atgatacctg cgtagagaac  1080
gagagcatat ttctcaattc tctgccaggg aatgaagctt ttttaaggtt gcttcggagc  1140
ggctattttg aagtgtttga cgtgtttgtg gtgcctgagc tgcatctgga cactccgggt  1200
cgagtggtcg ccgtcttgc tctgctggtg ttcatcctca acgatttaga cgctaattct  1260
gcttcttcag gctttgattc aggttttctc gtggaccgtc tctgcgtgcc gctatggctg  1320
```

```
aaggccaggg cgttcaagat cacccagagc tccaggagca cttcgcagcc ttcctcgtcg   1380
cccgacaaga cgacccagac taccagccag tagacgggga cagcccaccc cgggctagcc   1440
tggaggaggc tgaacagagc agcactcgtt tcgagcacat cagttaccga gacgtggtgg   1500
atgacttcaa tagatgccat gatgtttttt atgagaggta cagttttgag gacataaaga   1560
gctacgaggc tttgcctgag gacaatttgg agcagctcat agctatgcat gctaaaatca   1620
agctgctgcc cggtcgggag tatgagttga ctcaaccttt gaacataaca tcttgcgcct   1680
atgtgctcgg aaatggggct actattaggg taacagggga agcctccccg gctattagag   1740
tgggggccat ggccgtgggt ccgtgtgtaa caggaatgac tggggtgact tttgtgaatt   1800
gtaggtttga gagagagtca acaattaggg ggtccctgat acgagcttca actcacgtgc   1860
tgtttcatgg ctgttatttt atgggaatta tgggcacttg tattgaggtg ggggcgggag   1920
cttacattcg gggttgtgag tttgtgggct gttaccgggg aatctgttct acttctaaca   1980
gagatattaa ggtgaggcag tgcaactttg acaaatgctt actgggtatt acttgtaagg   2040
gggactatcg tctttcggga aatgtgtgtt ctgagacttt ctgctttgct catttagagg   2100
gagagggttt ggttaaaaac aacacagtca agtcccctag tcgctggacc agcgagtctg   2160
gcttttccat gataacttgt gcagacggca gggttacgcc tttgggttcc ctccacattg   2220
tgggcaaccg ttgtaggcgt tggccaacca tgcaggggaa tgtgtttatc atgtctaaac   2280
tgtatctggg caacagaata gggactgtag ccctgcccca gtgtgctttc tacaagtcca   2340
gcatttgttt ggaggagagg gcgacaaaca agctggtctt ggcttgtgct tttgagaata   2400
atgtactggt gtacaaagtg ctgagacggg agagtccctc aaccgtgaaa atgtgtgttt   2460
gtgggacttc tcattatgca aagcctttga cactggcaat tatttcttca gatattcggg   2520
ctaatcgata catgtacact gtggactcaa cagagttcac ttctgacgag gatt          2574
```

<210> SEQ ID NO 2
<211> LENGTH: 1245
<212> TYPE: DNA
<213> ORGANISM: artificial
<220> FEATURE:
<223> OTHER INFORMATION: Bovine adenovirus type 3 with E3 region
      deletion

<400> SEQUENCE: 2

```
ttgtaagact ctcctatctg tctctgtgct gcttttccgc ttcaagcccc acaagcatga    60
aggggtttct gctcatcttc agcctgcttg tgcattgtcc cctaattcat gttgggacca   120
ttagcttcta tgctgcaagg cccgggtctg agcctaacgc gacttatgtt tgtgactatg   180
gaagcgagtc agattacaac cccaccacgg ttctgtggtt ggctcgagag accgatggct   240
cctggatctc tgttcttttc cgtcacaacg gctcctcaac tgcagccccc ggggtcgtcg   300
cgcactttac tgaccacaac agcagcattg tggtccccca gtattacctc ctcaacaact   360
cactctctaa gctctgctgc tcataccggc acaacgagcg ttctcagttt acctgcaaac   420
aagctgacgt ccctacctgt cacgagcccg gcaagccgct caccctccgc gtctcccccg   480
cgctgggaac tgcccaccaa gcagtcactt ggttttttca aaatgtaccc atagctactg   540
tttaccgacc ttggggcaat gtaacttggt tttgtcctcc cttcatgtgt acctttaatg   600
tcagcctgaa ctccctactt atttacaact tttctgacaa aaccgggggg caatacacag   660
ctctcatgca ctccggacct gcttccctct ttcagtctct taagccaacg acttgtgtca   720
ccaaggtgga ggacccgccg tatgccaacg acccggcctc gcctgtgtgg cgcccactgc   780
```

```
ttttttgcctt cgtcctctgc accggctgcg cggtgttgtt aaccgccttc ggtccatcga    840
ttctatccgg tacccgaaag cttatctcag cccgcttttg gagtcccgag ccctatacca    900
ccctccacta acagtccccc catggagcca gacggagttc atgccgagca gcagtttatc    960
ctcaatcaga tttcctgcgc caacactgcc ctccagcgtc aaagggagga actagcttcc   1020
cttgtcatgt tgcatgcctg taagcgtggc ctcttttgtc cagtcaaaac ttacaagctc   1080
agcctcaacg cctcggccag cgagcacagc ctgcactttg aaaaaagtcc ctcccgattc   1140
accctggtca acactcacgc cggagcttct gtgcgagtgg ccctacacca ccagggagct   1200
tccggcagca tccgctgttc ctgttcccac gccgagtgcc tcccc                   1245
```

<210> SEQ ID NO 3
<211> LENGTH: 568
<212> TYPE: PRT
<213> ORGANISM: Influenza A virus (A/Hong Kong.156/97 (H5N1)

<400> SEQUENCE: 3

```
Met Glu Lys Thr Val Leu Leu Leu Ala Thr Val Ser Leu Val Lys Ser
1               5                  10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Arg Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
```

```
                290                 295                 300
Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
                370                 375                 380

Glu Ser Thr Gln Lys Ala Ile Asp Gly Val Thr Asn Lys Val Asn Ser
385                 390                 395                 400

Ile Ile Asn Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
                450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
                500                 505                 510

Arg Leu Asn Arg Glu Glu Ile Ser Gly Val Lys Leu Glu Ser Met Gly
                515                 520                 525

Thr Tyr Gln Ile Leu Ser Ile Tyr Ser Thr Val Ala Ser Ser Leu Ala
                530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 4
<211> LENGTH: 735
<212> TYPE: PRT
<213> ORGANISM: Foot-and-mouth disease virus

<400> SEQUENCE: 4

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
                20                  25                  30

Asn Ser Met Asp Thr Gln Leu Gly Asp Asn Ala Ile Ser Gly Gly Ser
                35                  40                  45

Asn Glu Gly Ser Thr Asp Thr Thr Ser Thr His Thr Thr Asn Thr Gln
                50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95
```

```
Glu Asp Arg Ile Leu Thr Thr Arg Asn Gly His Thr Thr Ser Thr Thr
                100                 105                 110
Gln Ser Ser Val Gly Val Thr Tyr Gly Tyr Ala Thr Ala Glu Asp Phe
            115                 120                 125
Val Ser Gly Pro Asn Thr Ser Gly Leu Glu Thr Arg Val Val Gln Ala
        130                 135                 140
Glu Arg Phe Phe Lys Thr His Leu Phe Asp Trp Val Thr Ser Asp Ser
145                 150                 155                 160
Phe Gly Arg Cys His Leu Leu Glu Leu Pro Thr Asp His Lys Gly Val
                165                 170                 175
Tyr Gly Ser Leu Thr Asp Ser Tyr Ala Tyr Met Arg Asn Gly Trp Asp
            180                 185                 190
Val Glu Val Thr Ala Val Gly Asn Gln Phe Asn Gly Gly Cys Leu Leu
        195                 200                 205
Val Ala Met Val Pro Glu Leu Cys Ser Ile Gln Lys Arg Glu Leu Tyr
    210                 215                 220
Gln Leu Thr Leu Phe Pro His Gln Phe Ile Asn Pro Arg Thr Asn Met
225                 230                 235                 240
Thr Ala His Ile Thr Val Pro Phe Val Gly Val Asn Arg Tyr Asp Gln
                245                 250                 255
Tyr Lys Val His Lys Pro Trp Thr Leu Val Val Met Val Val Ala Pro
            260                 265                 270
Leu Thr Val Asn Thr Glu Gly Ala Pro Gln Ile Lys Val Tyr Ala Asn
        275                 280                 285
Ile Ala Pro Thr Asn Val His Val Ala Gly Glu Phe Pro Ser Lys Glu
    290                 295                 300
Gly Ile Phe Pro Val Ala Cys Ser Asp Gly Tyr Gly Gly Leu Val Thr
305                 310                 315                 320
Thr Asp Pro Lys Thr Ala Asp Pro Val Tyr Gly Lys Val Phe Asn Pro
                325                 330                 335
Pro Arg Asn Gln Leu Pro Gly Arg Phe Thr Asn Leu Leu Asp Val Ala
            340                 345                 350
Glu Ala Cys Pro Thr Phe Leu Arg Phe Glu Gly Gly Val Pro Tyr Val
        355                 360                 365
Thr Thr Lys Thr Asp Ser Asp Arg Val Leu Ala Gln Phe Asp Met Ser
    370                 375                 380
Leu Ala Ala Lys His Met Ser Asn Thr Phe Leu Ala Gly Leu Ala Gln
385                 390                 395                 400
Tyr Tyr Thr Gln Tyr Ser Gly Thr Ile Asn Pro His Phe Met Phe Thr
                405                 410                 415
Gly Pro Thr Asp Ala Lys Ala Arg Tyr Met Ile Ala Tyr Ala Pro Pro
            420                 425                 430
Gly Met Glu Pro Pro Lys Thr Pro Glu Ala Ala His Cys Ile His
        435                 440                 445
Ala Glu Trp Asp Thr Gly Leu Asn Ser Lys Phe Thr Phe Ser Ile Pro
    450                 455                 460
Tyr Leu Ser Ala Ala Asp Tyr Ala Tyr Thr Ala Ser Asp Val Ala Glu
465                 470                 475                 480
Thr Thr Asn Val Gln Gly Trp Val Cys Leu Phe Gln Ile Thr His Gly
                485                 490                 495
Lys Ala Asp Gly Asp Ala Leu Val Val Leu Ala Ser Ala Gly Lys Asp
            500                 505                 510
Phe Glu Leu Arg Leu Pro Val Asp Ala Arg Ala Glu Thr Thr Ser Ala
```

```
                515                 520                 525
Gly Glu Ser Ala Asp Pro Val Thr Thr Thr Val Glu Asn Tyr Gly Gly
        530                 535                 540

Glu Thr Gln Ile Gln Arg Arg Gln His Thr Asp Val Ser Phe Ile Met
545                 550                 555                 560

Asp Arg Phe Val Lys Val Thr Pro Gln Asn Gln Ile Asn Ile Leu Asp
                565                 570                 575

Leu Met Gln Ile Pro Ser His Thr Leu Val Gly Ala Leu Leu Arg Ala
        580                 585                 590

Ser Thr Tyr Tyr Phe Ser Asp Leu Glu Ile Ala Val Lys His Glu Gly
                595                 600                 605

Asp Leu Thr Trp Val Pro Asn Gly Ala Pro Glu Lys Ala Leu Asp Asn
        610                 615                 620

Thr Thr Asn Pro Thr Ala Tyr His Lys Ala Pro Leu Thr Arg Leu Ala
625                 630                 635                 640

Leu Pro Tyr Thr Ala Pro His Arg Val Leu Ala Thr Val Tyr Asn Gly
                645                 650                 655

Glu Cys Arg Tyr Ser Arg Asn Ala Val Pro Asn Val Arg Gly Asp Leu
        660                 665                 670

Gln Val Leu Ala Gln Lys Val Arg Thr Leu Pro Thr Ser Phe Asn
        675                 680                 685

Tyr Gly Ala Ile Lys Ala Thr Arg Val Thr Glu Leu Leu Tyr Arg Met
        690                 695                 700

Lys Arg Ala Glu Thr Tyr Cys Pro Arg Pro Leu Leu Ala Ile His Pro
705                 710                 715                 720

Thr Glu Ala Arg His Lys Gln Lys Ile Val Ala Pro Val Lys Gln
                725                 730                 735

<210> SEQ ID NO 5
<211> LENGTH: 729
<212> TYPE: PRT
<213> ORGANISM: artificial
<220> FEATURE:
<223> OTHER INFORMATION: foot and mouse disease virus structural
      proteins separated by furin cleavage sites

<400> SEQUENCE: 5

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
                20                  25                  30

Asn Ser Met Asp Thr Gln Leu Gly Asp Asn Ala Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ala Phe Ser Gly Leu
65                  70                  75                  80

Phe Arg Arg His Arg Arg Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Thr Ala Glu Asp Phe
        115                 120                 125

Val Ser Gly Pro Asn Thr Ser Gly Leu Glu Thr Arg Val Val Gln Ala
    130                 135                 140
```

```
Glu Arg Phe Phe Lys Thr His Leu Phe Asp Trp Val Thr Asp Ser
145                 150                 155                 160

Phe Gly Arg Cys His Leu Leu Glu Leu Pro Thr Asp His Lys Gly Val
            165                 170                 175

Tyr Gly Ser Leu Thr Asp Ser Tyr Ala Tyr Met Arg Asn Gly Trp Asp
            180                 185                 190

Val Glu Val Thr Ala Val Gly Asn Gln Phe Asn Gly Gly Cys Leu Leu
        195                 200                 205

Val Ala Met Val Pro Glu Leu Cys Ser Ile Gln Lys Arg Glu Leu Tyr
    210                 215                 220

Gln Leu Thr Leu Phe Pro His Gln Phe Ile Asn Pro Arg Thr Asn Met
225                 230                 235                 240

Thr Ala His Ile Thr Val Pro Phe Val Gly Val Asn Arg Tyr Asp Gln
                245                 250                 255

Tyr Lys Val His Lys Pro Trp Thr Leu Val Met Val Val Ala Pro
            260                 265                 270

Leu Thr Val Asn Thr Glu Gly Ala Pro Gln Ile Lys Val Tyr Ala Asn
                275                 280                 285

Ile Ala Pro Thr Asn Arg Arg His Arg Arg Gly Ile Phe Pro Val Ala
    290                 295                 300

Cys Ser Asp Gly Tyr Gly Gly Leu Val Thr Thr Asp Pro Lys Thr Ala
305                 310                 315                 320

Asp Pro Val Tyr Gly Lys Val Phe Asn Pro Pro Arg Asn Gln Leu Pro
                325                 330                 335

Gly Arg Phe Thr Asn Leu Leu Asp Val Ala Glu Ala Cys Pro Thr Phe
            340                 345                 350

Leu Arg Phe Glu Gly Gly Val Pro Tyr Val Thr Thr Lys Thr Asp Ser
            355                 360                 365

Asp Arg Val Leu Ala Gln Phe Asp Met Ser Leu Ala Ala Lys His Met
        370                 375                 380

Ser Asn Thr Phe Leu Ala Gly Leu Ala Gln Tyr Tyr Thr Gln Tyr Ser
385                 390                 395                 400

Gly Thr Ile Asn Pro His Phe Met Phe Thr Gly Pro Thr Asp Ala Lys
                405                 410                 415

Ala Arg Tyr Met Ile Ala Tyr Ala Pro Pro Gly Met Glu Pro Pro Lys
            420                 425                 430

Thr Pro Glu Ala Ala Ala His Cys Ile His Ala Glu Trp Asp Thr Gly
        435                 440                 445

Leu Asn Ser Lys Phe Thr Phe Ser Ile Pro Tyr Leu Ser Ala Ala Asp
450                 455                 460

Tyr Ala Tyr Thr Ala Ser Asp Val Ala Glu Thr Thr Asn Val Gln Gly
465                 470                 475                 480

Trp Val Cys Leu Phe Gln Ile Thr His Gly Lys Ala Asp Gly Asp Ala
                485                 490                 495

Leu Val Val Leu Ala Ser Ala Gly Lys Asp Phe Glu Leu Arg Leu Pro
            500                 505                 510

Val Arg Arg His Arg Arg Thr Thr Ser Ala Gly Glu Ser Ala Asp Pro
    515                 520                 525

Val Thr Thr Val Glu Asn Tyr Gly Gly Glu Thr Gln Ile Gln Arg
    530                 535                 540

Arg Gln His Thr Asp Val Ser Phe Ile Met Asp Arg Phe Val Lys Val
545                 550                 555                 560

Thr Pro Gln Asn Gln Ile Asn Ile Leu Asp Leu Met Gln Ile Pro Ser
```

```
                565                 570                 575
His Thr Leu Val Gly Ala Leu Leu Arg Ala Ser Thr Tyr Tyr Phe Ser
            580                 585                 590

Asp Leu Glu Ile Ala Val Lys His Glu Gly Asp Leu Thr Trp Val Pro
            595                 600                 605

Asn Gly Ala Pro Glu Lys Ala Leu Asp Asn Thr Thr Asn Pro Thr Ala
            610                 615                 620

Tyr His Lys Ala Pro Leu Thr Arg Leu Ala Leu Pro Tyr Thr Ala Pro
625                 630                 635                 640

His Arg Val Leu Ala Thr Val Tyr Asn Gly Glu Cys Arg Tyr Ser Arg
                645                 650                 655

Asn Ala Val Pro Asn Val Arg Gly Asp Leu Gln Val Leu Ala Gln Lys
            660                 665                 670

Val Val Arg Thr Leu Pro Thr Ser Phe Asn Tyr Gly Ala Ile Lys Ala
                675                 680                 685

Thr Arg Val Thr Glu Leu Leu Tyr Arg Met Lys Arg Ala Glu Thr Tyr
            690                 695                 700

Cys Pro Arg Pro Leu Leu Ala Ile His Pro Thr Glu Ala Arg His Lys
705                 710                 715                 720

Gln Lys Ile Val Ala Pro Val Lys Gln
                725

<210> SEQ ID NO 6
<211> LENGTH: 5
<212> TYPE: PRT
<213> ORGANISM: artificial
<220> FEATURE:
<223> OTHER INFORMATION: furin cleavage domain

<400> SEQUENCE: 6

Arg Arg His Arg Arg
1               5

<210> SEQ ID NO 7
<211> LENGTH: 960
<212> TYPE: DNA
<213> ORGANISM: Influenza A virus (A/Hong Kong/156/97(H5N1))

<400> SEQUENCE: 7
ctgtcaaaat ggagaaaaca gtgcttcttc ttgcaacagt cagtcttgtt aaaagtgatc      60
agatttgcat tggttaccat gcaaacaact cgacagagca ggttgacaca ataatggaaa     120
agaatgttac tgttacacat gcccaagaca tactggaaag gacacacaac gggaagctct     180
gcgatctaaa tggagtgaag cctctcattt tgagggattg tagtgtagct ggatggctcc     240
tcggaaaccc tatgtgtgac gaattcatca atgtgccgga atggtcttac atagtggaga     300
aggccagtcc agccaatgac ctctgttatc cagggaattt caacgactat gaagaactga     360
aacacctatt gagcagaata accattttg agaaaatcca gatcatcccc aaaagttctt     420
ggtccaatca tgatgcctca tcaggggtga gctcagcatg tccatacctt ggaggtcct      480 ccttttcag aaatgtggta tggcttatca aaaagaacag tgcatacca acaataaaga      540 ggagctacaa taataccaac caagaagatc ttttggtact gtgggggatt caccatccta     600
atgatgcggc agagcagaca aagctctatc aaaatccaac cacctacatt tccgttggaa     660
catcaacact gaaccagaga ttggttccag aaatagctac tagacccaa gtaaacgggc      720 aaagtggaag aatggagttc ttctggacaa ttttaaagcc gaatgatgcc atcaatttcg     780
```

```
agagtaatgg aaatttcatt gctccagaat atgcatacaa aattgtcaag aaaggggact    840
caacaattat gaaaagtgaa ttggaatatg gtaactgcaa caccaagtgt caaactccaa    900 tggggggcgat aaactctagt atgccattcc acaacataca ccccctcacc atcggggaat    960
```

<210> SEQ ID NO 8
<211> LENGTH: 2244
<212> TYPE: DNA
<213> ORGANISM: artificial
<220> FEATURE:
<223> OTHER INFORMATION: DNA sequence of Foot-and-mouth disease virus P1
      gene with furin cleavage site inserted and bovine codon optimized

<400> SEQUENCE: 8

```
atgcaggggac ctactctggc tgtgctgggg gctctgctgg ccgtcgccgt ctctatgggg     60
gctggacagt cttcacccgc taccggaagt cagaaccagt cagggaacac aggatctatc    120
atcaacaact actacatgca gcagtaccag aacagtatgg acactcagct gggagataac    180
gccatctccg gcgggtctaa tgagggctca actgatacca caagcaccca cactaccaat    240
acacagaaca atgactggtt cagcaagctg gctagctccg ccttctccgg cctgtttcgg    300
aggcaccgca gagataagaa aaccgaggaa acaactctgc tggaggacag aattctgacc    360
acacgaaacg ggcatactac ctccacaact cagtctagtg tgggagtcac ttacggctat    420
gctaccgccg aagctttgt gtccggcccc aatacatctg gactggagac tcgggtggtc    480
caggctgaaa ggttctttaa gactcacctg ttcgactggg tgacctcaga tagctttggc    540
agatgccacc tgctggagct gcctacagac cataaaggcg tgtacgggag cctgactgat    600
tcctacgctt atatgcggaa cggatgggac gtggaagtca ccgctgtggg aaaccagttc    660
aatggaggat gcctgctggt ggctatggtc ccagagctgt gttccatcca agagagaa    720 ctgtatcagc tgaccctgtt cccacaccag tttatcaacc cccgaacaaa tatgactgcc    780
catattacag tgccttttgt gggcgtcaac cgctacgacc agtataaggt gcacaaacca    840
tggaccctgg tggtcatggt ggtcgctcca ctgaccgtga atacagaggg cgccccccag    900
atcaaggtct acgctaacat tgctccaacc aatcgacgac acaggcgagg aatcttccct    960
gtggcttgca gcgacggata cggaggactg gtgaccacag accccaagac cgccgatcct   1020
gtgtatggga agtcttcaa ccccctcgc aatcagctgc ccggaagatt tactaacctg   1080
ctggatgtgg ctgaggcctg tcctaccttc ctgagatttg aaggcggggt gccatacgtc   1140
actaccaaga ccgactccga tcgggtgctg gcccagttcg acatgagtct ggccgctaaa   1200
cacatgtcaa acacctttct ggctggactg gcccagtact atacccagta tagcggcaca   1260
atcaatcctc atttcatgtt tactgggcca accgatgcta aggcccggta catgattgct   1320
tatgccccac ccgggatgga gcctccaaaa accctgaag ccgctgccca ctgcatccat   1380
gccgagtggg acacaggact gaacagtaag ttcactttt caattccata cctgagcgct   1440
gccgactacg cttataccgc ctccgatgtg ccgagacaa ctaatgtgca gggctgggtc   1500
tgtctgttcc agatcacaca cgggaaggct gacggagatg ccctggtggt cctggctagc   1560
gccggaaaag atttgagct gaggctgccc gtgagacgac atcggaggac cacatctgct   1620
ggcgaaagtg ccgaccctgt gactaccaca gtcgagaact acgaggcga aactcagatc   1680 cagcgcagac agcacaccga cgtgtcattc attatggata ggtttgtgaa ggtcaccca   1740 cagaaccaga tcaatattct ggatctgatg cagatcccct ctcacaccct ggtgggagct   1800
ctgctgcgag cttccacata ctatttctct gatctggaga ttgccgtgaa acatgaagga   1860
```

-continued

```
gacctgacct gggtcccaaa cggagctcca gagaaggctc tggacaacac taccaatccc    1920
acagcttacc acaaagcccc tctgacccga ctggctctgc cttatacagc cccacatcgg    1980
gtgctggcca ccgtctacaa cggcgagtgc cgatatagtc ggaacgctgt gccaaatgtc    2040 agggggatc tgcaggtgct ggcccagaag gtggtccgca cactgcccac ttctttcaac     2100
tacggcgcta tcaaggccac cagggtgaca gagctgctgt acaggatgaa acgcgccgaa    2160
acctattgtc cccgccctct gctggccatc caccctacag aagccagaca taaacagaaa    2220
atcgtcgctc cagtgaaaca gtga                                           2244
```

<210> SEQ ID NO 9
<211> LENGTH: 747
<212> TYPE: PRT
<213> ORGANISM: artificial
<220> FEATURE:
<223> OTHER INFORMATION: protein sequence of Foot-and-mouth disease
      virus P1 with furin cleavage site

<400> SEQUENCE: 9

```
Met Gln Gly Pro Thr Leu Ala Val Leu Gly Ala Leu Leu Ala Val Ala
1               5                   10                  15

Val Ser Met Gly Ala Gly Gln Ser Ser Pro Ala Thr Gly Ser Gln Asn
            20                  25                  30

Gln Ser Gly Asn Thr Gly Ser Ile Ile Asn Asn Tyr Tyr Met Gln Gln
        35                  40                  45

Tyr Gln Asn Ser Met Asp Thr Gln Leu Gly Asp Asn Ala Ile Ser Gly
    50                  55                  60

Gly Ser Asn Glu Gly Ser Thr Asp Thr Thr Ser Thr His Thr Thr Asn
65                  70                  75                  80

Thr Gln Asn Asn Asp Trp Phe Ser Lys Leu Ala Ser Ser Ala Phe Ser
                85                  90                  95

Gly Leu Phe Arg Arg His Arg Arg Asp Lys Lys Thr Glu Glu Thr Thr
            100                 105                 110

Leu Leu Glu Asp Arg Ile Leu Thr Thr Arg Asn Gly His Thr Thr Ser
        115                 120                 125

Thr Thr Gln Ser Ser Val Gly Val Thr Tyr Gly Tyr Ala Thr Ala Glu
    130                 135                 140

Asp Phe Val Ser Gly Pro Asn Thr Ser Gly Leu Glu Thr Arg Val Val
145                 150                 155                 160

Gln Ala Glu Arg Phe Phe Lys Thr His Leu Phe Asp Trp Val Thr Ser
                165                 170                 175

Asp Ser Phe Gly Arg Cys His Leu Leu Glu Leu Pro Thr Asp His Lys
            180                 185                 190

Gly Val Tyr Gly Ser Leu Thr Asp Ser Tyr Ala Tyr Met Arg Asn Gly
        195                 200                 205

Trp Asp Val Glu Val Thr Ala Val Gly Asn Gln Phe Asn Gly Gly Cys
    210                 215                 220

Leu Leu Val Ala Met Val Pro Glu Leu Cys Ser Ile Gln Lys Arg Glu
225                 230                 235                 240

Leu Tyr Gln Leu Thr Leu Phe Pro His Gln Phe Ile Asn Pro Arg Thr
                245                 250                 255

Asn Met Thr Ala His Ile Thr Val Pro Phe Val Gly Val Asn Arg Tyr
            260                 265                 270

Asp Gln Tyr Lys Val His Lys Pro Trp Thr Leu Val Val Met Val Val
        275                 280                 285
```

```
Ala Pro Leu Thr Val Asn Thr Glu Gly Ala Pro Gln Ile Lys Val Tyr
    290                 295                 300
Ala Asn Ile Ala Pro Thr Asn Arg Arg His Arg Arg Gly Ile Phe Pro
305                 310                 315                 320
Val Ala Cys Ser Asp Gly Tyr Gly Leu Val Thr Thr Asp Pro Lys
            325                 330                 335
Thr Ala Asp Pro Val Tyr Gly Lys Val Phe Asn Pro Arg Asn Gln
        340                 345                 350
Leu Pro Gly Arg Phe Thr Asn Leu Leu Asp Val Ala Glu Ala Cys Pro
        355                 360                 365
Thr Phe Leu Arg Phe Glu Gly Gly Val Pro Tyr Val Thr Thr Lys Thr
370                 375                 380
Asp Ser Asp Arg Val Leu Ala Gln Phe Asp Met Ser Leu Ala Ala Lys
385                 390                 395                 400
His Met Ser Asn Thr Phe Leu Ala Gly Leu Ala Gln Tyr Tyr Thr Gln
                405                 410                 415
Tyr Ser Gly Thr Ile Asn Pro His Phe Met Phe Thr Gly Pro Thr Asp
            420                 425                 430
Ala Lys Ala Arg Tyr Met Ile Ala Tyr Ala Pro Pro Gly Met Glu Pro
        435                 440                 445
Pro Lys Thr Pro Glu Ala Ala Ala His Cys Ile His Ala Glu Trp Asp
    450                 455                 460
Thr Gly Leu Asn Ser Lys Phe Thr Phe Ser Ile Pro Tyr Leu Ser Ala
465                 470                 475                 480
Ala Asp Tyr Ala Tyr Thr Ala Ser Asp Val Ala Glu Thr Thr Asn Val
                485                 490                 495
Gln Gly Trp Val Cys Leu Phe Gln Ile Thr His Gly Lys Ala Asp Gly
            500                 505                 510
Asp Ala Leu Val Val Leu Ala Ser Ala Gly Lys Asp Phe Glu Leu Arg
        515                 520                 525
Leu Pro Val Arg Arg His Arg Arg Thr Thr Ser Ala Gly Glu Ser Ala
    530                 535                 540
Asp Pro Val Thr Thr Thr Val Glu Asn Tyr Gly Gly Glu Thr Gln Ile
545                 550                 555                 560
Gln Arg Arg Gln His Thr Asp Val Ser Phe Ile Met Asp Arg Phe Val
                565                 570                 575
Lys Val Thr Pro Gln Asn Gln Ile Asn Ile Leu Asp Leu Met Gln Ile
            580                 585                 590
Pro Ser His Thr Leu Val Gly Ala Leu Leu Arg Ala Ser Thr Tyr Tyr
        595                 600                 605
Phe Ser Asp Leu Glu Ile Ala Val Lys His Glu Gly Asp Leu Thr Trp
610                 615                 620
Val Pro Asn Gly Ala Pro Glu Lys Ala Leu Asp Asn Thr Thr Asn Pro
625                 630                 635                 640
Thr Ala Tyr His Lys Ala Pro Leu Thr Arg Leu Ala Leu Pro Tyr Thr
                645                 650                 655
Ala Pro His Arg Val Leu Ala Thr Val Tyr Asn Gly Glu Cys Arg Tyr
            660                 665                 670
Ser Arg Asn Ala Val Pro Asn Val Arg Gly Asp Leu Gln Val Leu Ala
        675                 680                 685
Gln Lys Val Val Arg Thr Leu Pro Thr Ser Phe Asn Tyr Gly Ala Ile
    690                 695                 700
Lys Ala Thr Arg Val Thr Glu Leu Leu Tyr Arg Met Lys Arg Ala Glu
```

-continued

```
        705                 710                 715                 720
Thr Tyr Cys Pro Arg Pro Leu Leu Ala Ile His Pro Thr Glu Ala Arg
                    725                 730                 735

His Lys Gln Lys Ile Val Ala Pro Val Lys Gln
                740                 745
```

ADENOVIRAL VECTOR SYSTEM FOR GENE DELIVERY

CROSS-REFERENCE

This application claims the benefit of U.S. provisional application 62/646,936, filed on Mar. 23, 2018. The content of which is expressly incorporated herein by reference entirely.

GOVERNMENT RIGHTS

This invention was made with government support under AI059374 awarded by National Institute of Health. The government has certain rights in the invention.

FIELD OF INVENTION

This disclosure relates to a novel adenoviral vector's construction and its uses thereof. Particularly, it relates to a unique cell line system to generate a novel bovine adenovirus vector that provides more gene insertion capabilities and better immunogenicity for inserted antigens. The unique cell line is used for generating and growing of the new adenovirus vectors for gene delivery or recombinant vaccine production.

BACKGROUND

Adenovirus (AdV) vector-based vaccines have been shown to elicit a balanced humoral and cell mediated immune (CMI) responses by activating innate immunity through both Toll-like receptor (TLR)-dependent as well as TLR-independent pathways. Due to the high prevalence of AdV in humans, the development of AdV-specific neutralizing antibodies, known as 'pre-existing vector immunity', is one of the potential concerns for several human AdV (HAdV) vector-based vaccine delivery systems. To address this concern, a number of less prevalent HAdVs or nonhuman AdVs have been developed as vaccine delivery vectors. These nonhuman AdV vectors are based on bovine AdV (BAdV), simian AdV (SAdV), porcine AdV (PAdV), ovine AdV (OAdV), Canine AdV (CAdV), avian AdV (AAdV) and murine AdV (MAdV). It has been demonstrated that there were no reductions in humoral and CMI responses against the vaccine immunogen and the resultant protection efficacy of a BAdV type 3 (BAdV-3) vector based H5N1 influenza vaccine even in the presence of exceptionally high levels of pre-existing HAdV vector immunity. In addition, pre-existing HAdV-neutralizing antibodies in humans did not cross-neutralize BAdV-3, and HAdV-specific CMI responses did not cross-react with BAdV-3. Bio-distribution, pathogenesis, transduction, and persistence studies in animal models and cell lines have suggested that the safety aspects of BAdV vectors are similar to that of HAdV vectors. It has been illustrated that the cell internalization of BAdV-3 is independent of the HAdV type C5 (HAdV-C5) receptors [Coxackievirus-AdV receptor (CAR) and $\alpha v \beta 3$ or $\alpha v \beta 5$ integrin], but it is indicated that the $\alpha(2,3)$-linked and $\alpha(2,6)$-linked sialic acid receptors serve as major receptors for BAdV-3 internalization. It appears that BAdV based vectors may serve as excellent vaccine vectors for humans without any concerns of pre-existing HAdV vector immunity.

However, in the current version of bovine adenovirus vector system, only about 0.6 kb deletion in the E1 region (only E1A) of bovine adenovirus genome can be made in a bovine cell line expressing human adenoviral E1 gene products. In addition, 1.2 Kb E3 deletion can easily be made in bovine adenovirus genome since E3 proteins are not essential for bovine adenovirus replication. Repeated efforts to expand the E1 deletion to both E1A and E1B regions were unsuccessful since human E1B proteins do not complement bovine adenovirus E1B proteins' functions. Therefore, there is a need to generate a new cell line that could support the replication of bovine adenovirus vector having full E1 deletion (E1A and E1B) with or without E3 deletion. Bovine adenovirus vectors having full E1 and E3 deletions can accommodate larger size foreign gene insert to provide more flexibility of gene expression.

SUMMARY OF THE INVENTION

In the current version of bovine adenoviral vector system, only 0.6 kb deletion in the E1 region of bovine adenoviral vector can be made in a bovine cell line that expresses human adenoviral E1 gene products. This disclosure provides a unique cell line that efficiently supports the replication of bovine adenoviral vector having the full E1 region deletion with or without E3 deletion, thereby extending the foreign gene cassette insertion capacity by at least 2 Kb. Such deletion would allow insertions up to 5.5 Kb foreign gene cassette containing one or more genes. This next generation of bovine adenoviral vectors and the unique cell line that expresses appropriate E1 gene products enhances the utility as well as acceptability of this vector system. This vector system can be used in both recombinant vaccine development and gene therapy applications.

A bovine adenovirus vector type 3 with all of its E1 region and E3 region deleted is provided in this disclosure.

A bovine adenovirus vector type 3 with all of its E1 region and E3 region deleted and replaced by at least one foreign gene up to 5.5 kb for expression can be created under this disclosure.

This disclosure provides a gene delivery system or a vaccine production system. The system comprises a bovine or equivalent cell line transfected with human adenovirus (HAdV) E1 region and bovine adenovirus EB1L gene (or E1BS and E1BL genes), and a bovine adenovirus vector type 3 (BAdV3) with E1A, E1BS, E1BL and E3 regions deletion and one or more targeted genes or antigenic domains for gene delivery.

In some preferred embodiment the aforementioned vaccine production system expresses hemagglutinin (HA) gene of an influenza virus.

In some preferred embodiment the aforementioned bovine cell line is a BHH3 that supports replication of E1, E3-deleted BAd3 vectors.

In some preferred embodiment the aforementioned bovine cell line is FBRT-HE1-BE1B/Full (FBRT-HE1 fetal bovine retinal cells that expresses HAdV-5 E1A, E1B-S and E1BL proteins and BAdV-3 E1B-L protein), FBRT-HE1-BE1BL, BHH3-E1BL, or BHH3-E1B/Full.

In some preferred embodiment the aforementioned vaccine production system expresses and processes VP2 protein of Foot and Mouse Disease virus (FMDV) from the P1 gene product.

The disclosure also provides a method of generating immunogenicity against H5NA influenza virus HA antigen in a subject. The method comprising administering to the subject an effective amount of BAdV3 vaccine vector expressing H5HA. In some preferred embodiment, the dose of such BAdV3 vaccine vector is at least 100 fold less than a human adenovirus (HAdV) counterpart expressing the same H5HA.

These and other features, aspects and advantages of the present invention will become better understood with reference to the following figures, associated descriptions and claims.

BRIEF DESCRIPTION OF THE SEQUENCE LISTING

SEQ ID NO:1 Bovine adenovirus type 3 with E1 region deletion

SEQ ID NO:2 Bovine adenovirus type 3 with E3 region deletion

SEQ ID NO:3 amino acid sequence of Influenza A virus (A/Hong Kong. 156/97 (H5N1) hemagglutinin subtype H5 (H5) gene SEQ ID NO:4 Foot-and-mouth disease virus P1 protein sequence SEQ ID NO:5 modified Foot-and-mouth disease virus P1 protein sequence with Furin cleavage site SEQ ID NO:6 Furin cleavage site SEQ ID NO:7 DNA sequence of Influenza A virus (A/Hong Kong. 156/97 (H5N1) hem agglutinin subtype H5 (H5) gene SEQ ID NO:8 DNA sequence of Foot-and-mouth disease virus P1 gene with furin cleavage site inserted and bovine codon optimized.

SEQ ID NO:9 protein sequence of Foot-and-mouth disease virus P1 with furin cleavage site

BRIEF DESCRIPTION OF THE DRAWINGS

FIG. 1. HA-specific serum IgG antibody responses in mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, serum samples were collected, diluted to 1:500, and the development of HA-specific IgG antibody responses were monitored by ELISA. Data are represented as the mean±standard deviation (SD) of the optical density (OD) readings. Statistically significant responses are shown as compared to PBS group (+) or i.n. versus i.m. route of inoculation in the same group (*). * or +, significant at $p<0.05$;  or ++, significant at $p<0.01$; * or +++, significant at $p<0.001$; and **** or ++++; significant at $p<0.0001$. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at $p>0.05$.

FIG. 2. HA-specific serum IgG1 antibody responses in mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, serum samples were collected, diluted to 1:500, and the development of HA-specific IgG antibody responses were monitored by ELISA. Data are represented as the mean±standard deviation (SD) of the optical density (OD) readings. Statistically significant responses are shown as compared to PBS group (+) or i.n. versus i.m. route of inoculation in the same group (*). * or +, significant at $p<0.05$;  or ++, significant at $p<0.01$; * or +++, significant at $p<0.001$; and **** or ++++; significant at $p<0.0001$. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at $p>0.05$.

FIG. 3. HA-specific serum IgG2a antibody responses in mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, serum samples were collected, diluted to 1:500, and the development of HA-specific IgG antibody responses were monitored by ELISA. Data are represented as the mean±standard deviation (SD) of the optical density (OD) readings. Statistically significant responses are shown as compared to PBS group (+) or i.n. versus i.m. route of inoculation in the same group (*). * or +, significant at $p<0.05$;  or ++, significant at $p<0.01$; * or +++, significant at $p<0.001$; and **** or ++++; significant at $p<0.0001$. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at $p>0.05$.

FIG. 4. HA-specific serum IgG2b antibody responses in mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, serum samples were collected, diluted to 1:500, and the development of HA-specific IgG antibody responses were monitored by ELISA. Data are represented as the mean±standard deviation (SD) of the optical density (OD) readings. Statistically significant responses are shown as compared to PBS group (+) or i.n. versus i.m. route of inoculation in the same group (*). * or +, significant at $p<0.05$;  or ++, significant at $p<0.01$; * or +++, significant at $p<0.001$; and **** or ++++; significant at $p<0.0001$. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at p>0.05.

Figure 5:
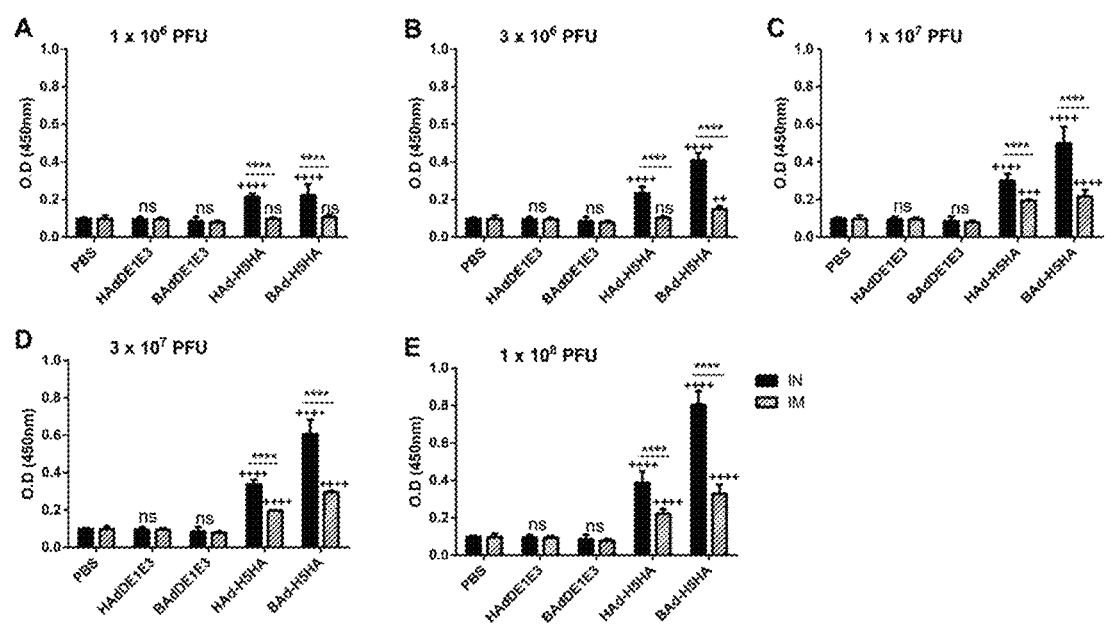

FIG. 5. HA-specific IgA antibody responses in nasal washes of mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, nasal wash samples were collected, diluted to 1:5, and the development of HA-specific IgG antibody responses were monitored by ELISA. Data are represented as the mean±standard deviation (SD) of the optical density (OD) readings. Statistically significant responses are shown as compared to PBS group (+) or i.n. versus i.m. route of inoculation in the same group (*). * or +, significant at p<0.05;  or ++, significant at p<0.01; * or +++, significant at p<0.001; and **** or ++++; significant at p<0.0001. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at p>0.05.

Figure 6:
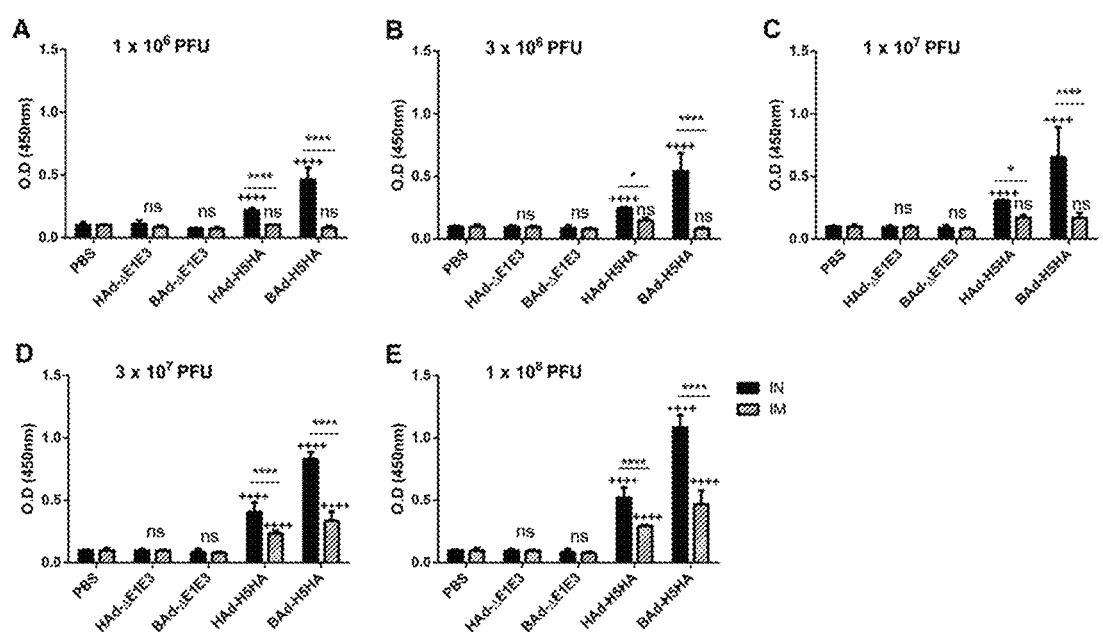

FIG. 6. HA-specific IgA antibody responses in lung washes of mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, lung wash samples were collected, diluted to 1:10, and the development of HA-specific IgG antibody responses were monitored by ELISA. Data are represented as the mean±standard deviation (SD) of the optical density (OD) readings. Statistically significant responses are shown as compared to PBS group (+) or i.n. versus i.m. route of inoculation in the same group (*). * or +, significant at p<0.05;  or ++, significant at p<0.01; * or +++, significant at p<0.001; and **** or ++++; significant at p<0.0001. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at p>0.05.

Figure 7:
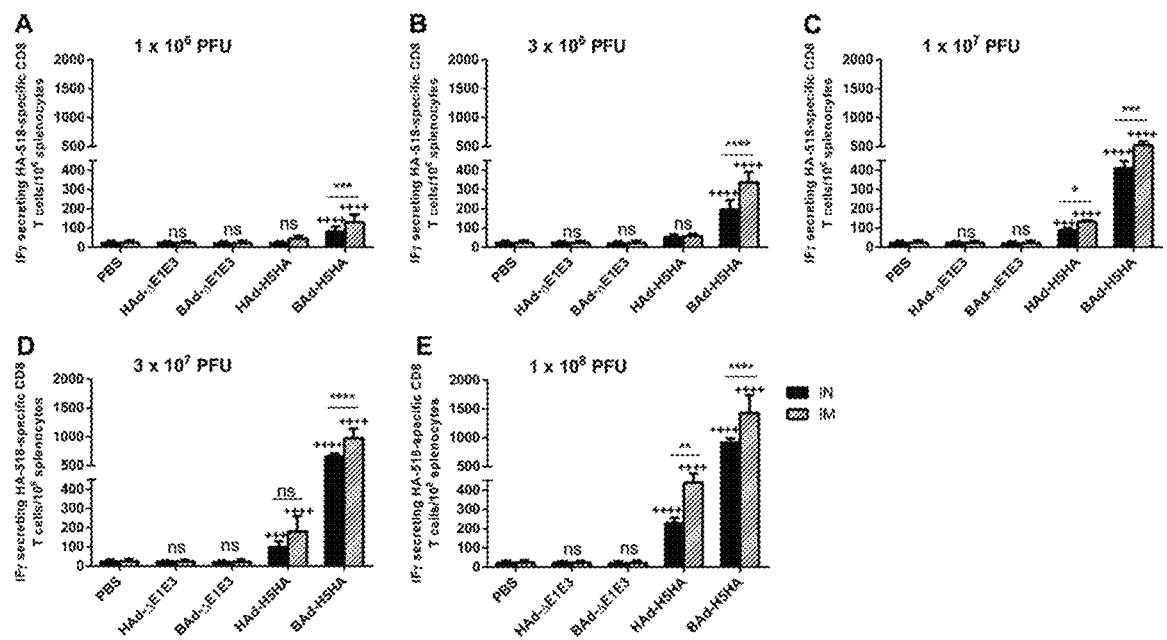

FIG. 7. HA518 epitope-specific IFNγ secreting CD8+ T cells in the spleens of mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, the spleens were collected, and the splenocytes were evaluated for HA-specific cell-mediated immune responses using IFNγ-ELISpot assay. The data represent mean±standard deviation (SD) of the number of spot-forming units (SFU). Statistically significant responses are shown as compared to PBS group (+) or i.n. versus i.m. route of inoculation in the same group (*). * or +, significant at p<0.05;  or ++, significant at p<0.01; * or +++, significant at p<0.001; and **** or ++++; significant at p<0.0001. The statistical analysis was done by Bonferroni post-test and two-way ANOVA using Graph Pad Prim 6. BAd-H5HA, bovine adenoviral vector expressing hemagglutinin (HA) of A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; and ns, no significance at p>0.05.

Figure 8:
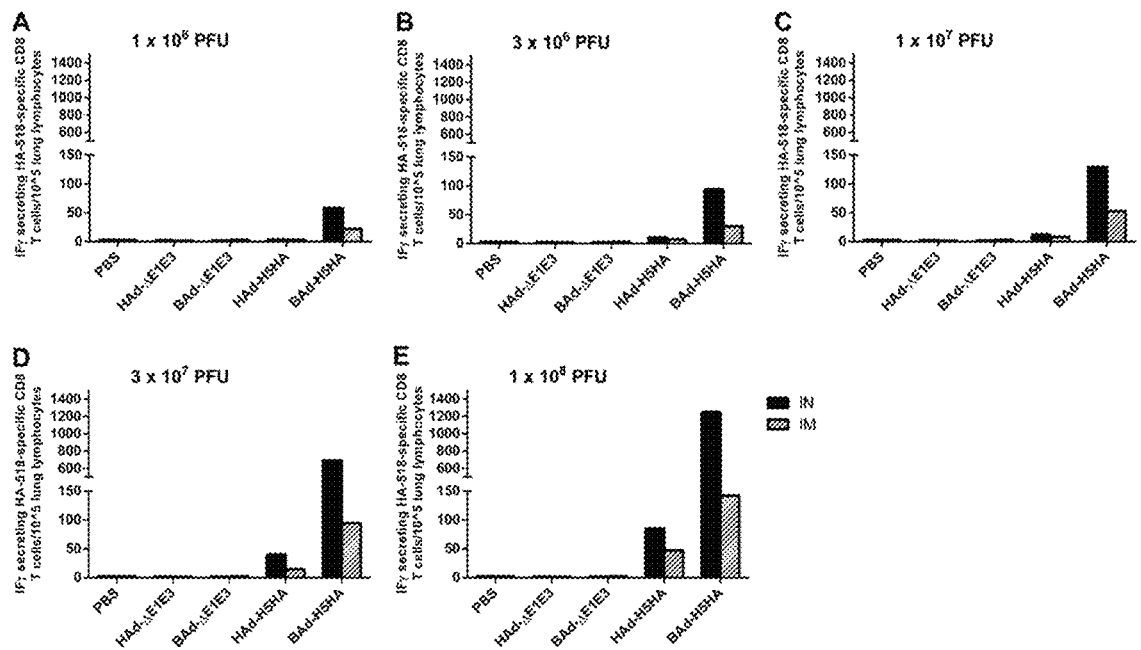

FIG. 8. HA518 epitope-specific IFNγ secreting CD8+ T cells in the respiratory lymph nodes (RLN) of mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, the RLN were collected, and the pooled RLN cells were evaluated for HA-specific cell-mediated immune responses using IFNγ-ELISpot assay. The data represent mean number of spot-forming units (SFU) from pooled samples. BAd-H5HA, bovine adenoviral vector expressing hemagglutinin (HA) of a A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline.

Figure 9:
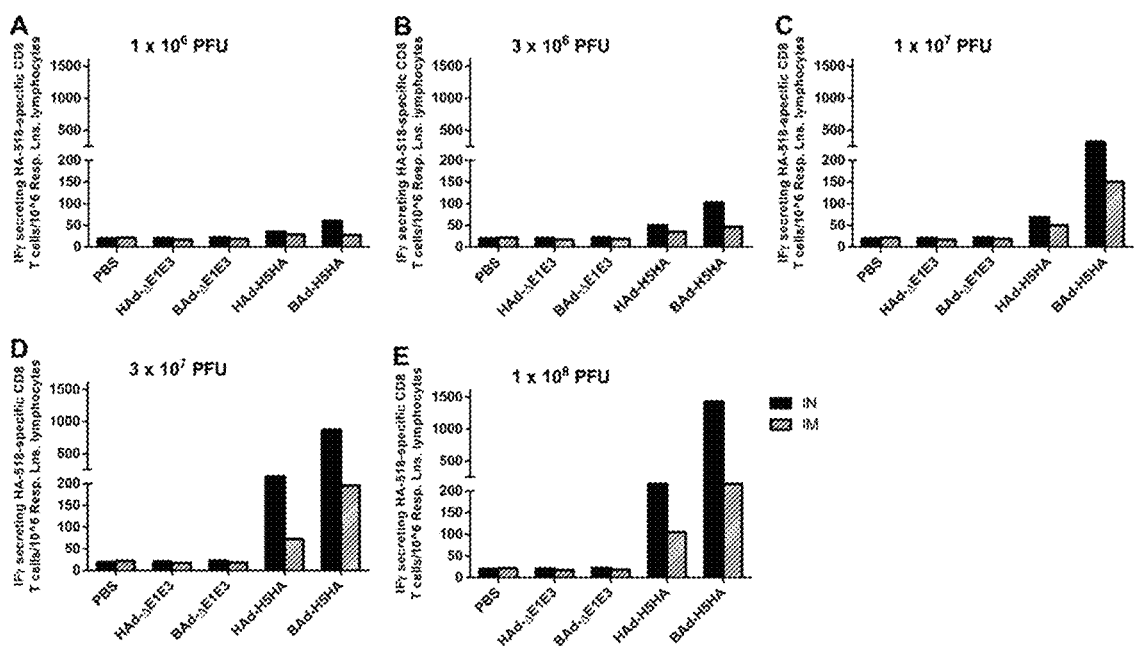

FIG. 9. HA518 epitope-specific IFNγ secreting CD8+ T cells in the inguinal lymph nodes (ILN) of mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, the ILN were collected, and the pooled ILN cells were evaluated for HA-specific cell-mediated immune responses using IFNγ-ELISpot assay. The data represent mean number of spot-forming units (SFU) from pooled samples. BAd-H5HA, bovine adenoviral vector expressing hemagglutinin (HA) of a A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline.

Figure 10:
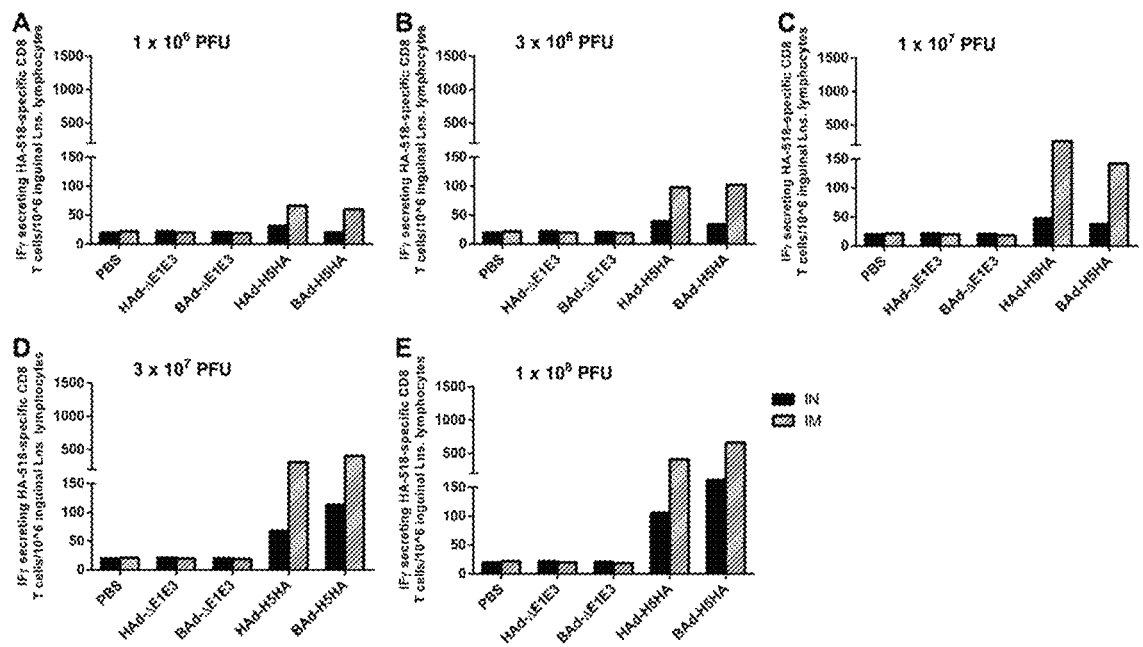

FIG. 10. HA518 epitope-specific IFNγ secreting CD8+ T cells in the lungs of mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after inoculation, the lungs were collected, and the pooled lung lymphocytes were evaluated for HA-specific cell-mediated immune responses using IFNγ-ELISpot assay. The data represent mean the number of spot-forming units (SFU) from pooled samples. BAd-H5HA, bovine adenoviral vector expressing hemagglutinin (HA) of a A/Hong Kong/

156/97(H5N1) influenza virus; HAd-H5HA, human adenoviral vector expressing HA of a A/Hong Kong/156/97 (H5N1) influenza virus; BAd-ΔE1E3 (BAd empty vector); HAd-ΔE1E3, (HAd empty vector); PBS, phosphate-buffered saline.

Figure 11:
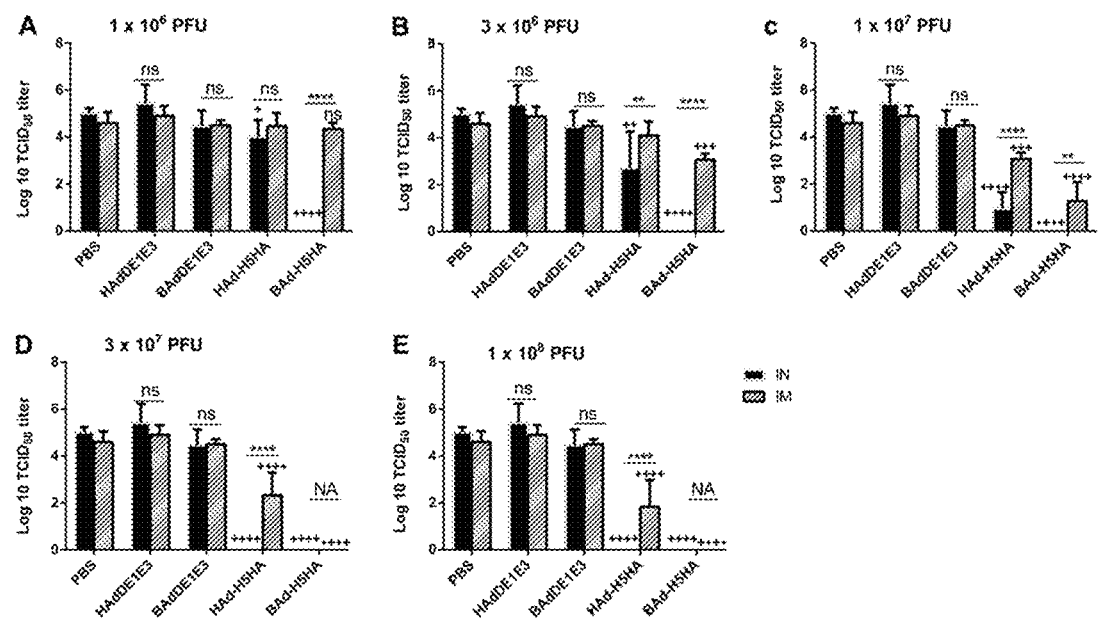

FIG. 11. Lung influenza virus titers in mice immunized once with BAd-H5HA or HAd-H5HA. Mice were immunized intramuscularly (i.m.) or intranasally (i.n.) once with $1\times10^6$ (A), $3\times10^6$ (B), $1\times10^7$ (C), $3\times10^7$ (D) or $1\times10^8$ (E) PFU of BAd-H5HA or HAd-H5HA. For all dose groups, mice inoculated i.m. or i.n. with PBS or $1\times10^8$ PFU of BAd-ΔE1E3 or HAd-ΔE1E3 served as negative or internal controls, respectively. Four weeks after immunization, mice were challenged with 100 $MID_{50}$ of A/Vietnam/1203/2004 (H5N1)-PR8/CDC-RG influenza virus, and three days after the challenged, mice were euthanized, and the lungs were collected to determine lung virus titers. The data are shown as mean Logo) $TCID_{50}\pm SD$ and the detection limit was 0.5 $Log_{10}$ $TCID_{50}$/ml. Statistically significant responses are shown as compared to PBS group (+) or i.n. versus i.m. route of inoculation in the same group (*). * or +, significant at $p<0.05$;  or ++, significant at $p<0.01$; * or +++, significant at $p<0.001$; and **** or ++++, significant at $p<0.0001$. The statistical analyses were done by Bonferroni post-test and two-way ANOVA using Graph Pad Prim 6. BAd-H5HA, bovine adenoviral vector expressing hemagglutinin (HA) of a A/Hong Kong/156/97(H5N1) influenza virus; HAd-H5HA, human adenoviral vector expressing HA of a A/Hong Kong/156/97(H5N1) influenza virus; BAd-ΔE1E3 (BAd empty vector); HAd-ΔE1E3, (HAd empty vector); PBS, phosphate-buffered saline; ns, no significance at $p>0.05$; NA, not applicable.

Figure 12:
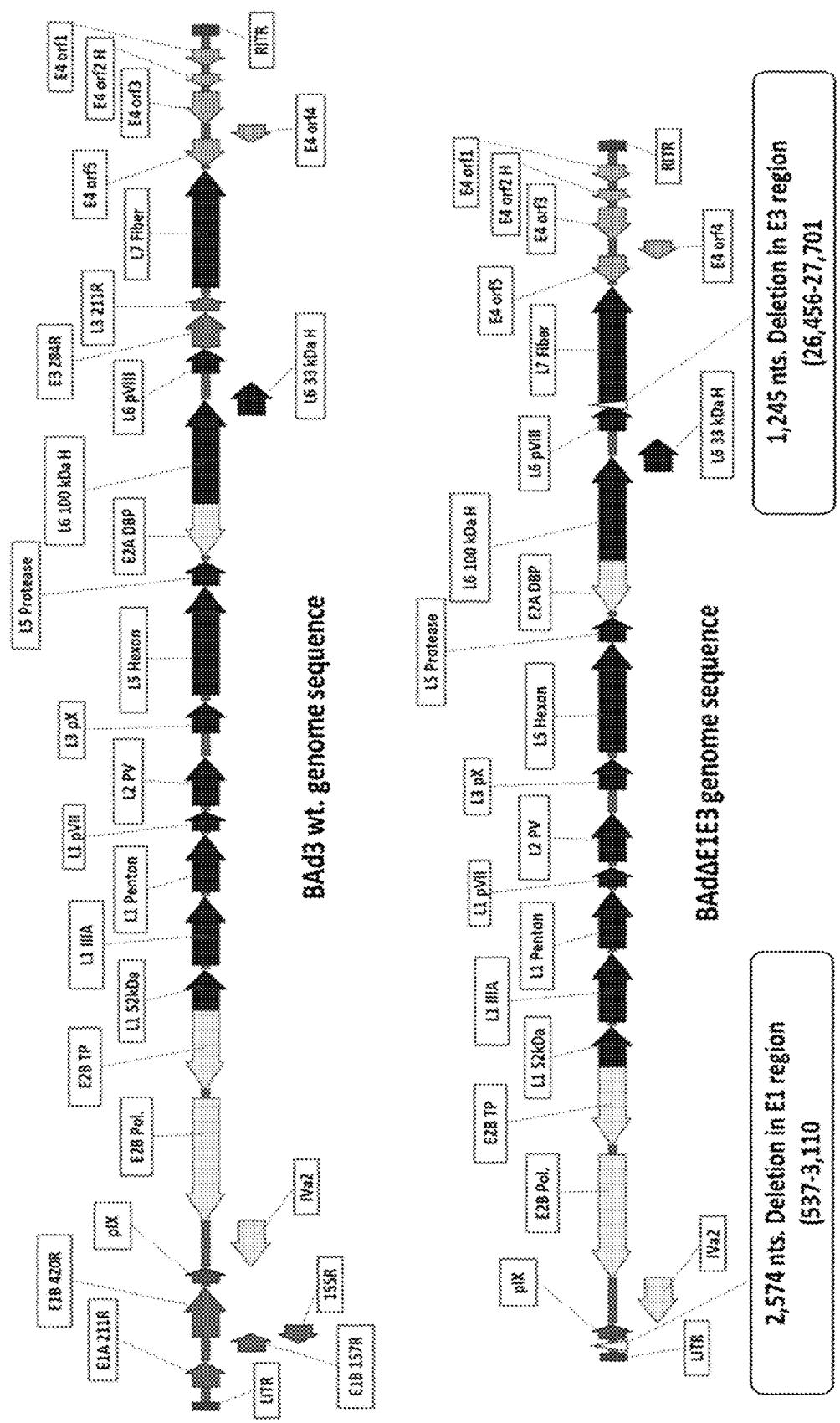

FIG. 12. Genomic map of BAdV3 wild type and ΔE1E3 deletions.

Figure 13:
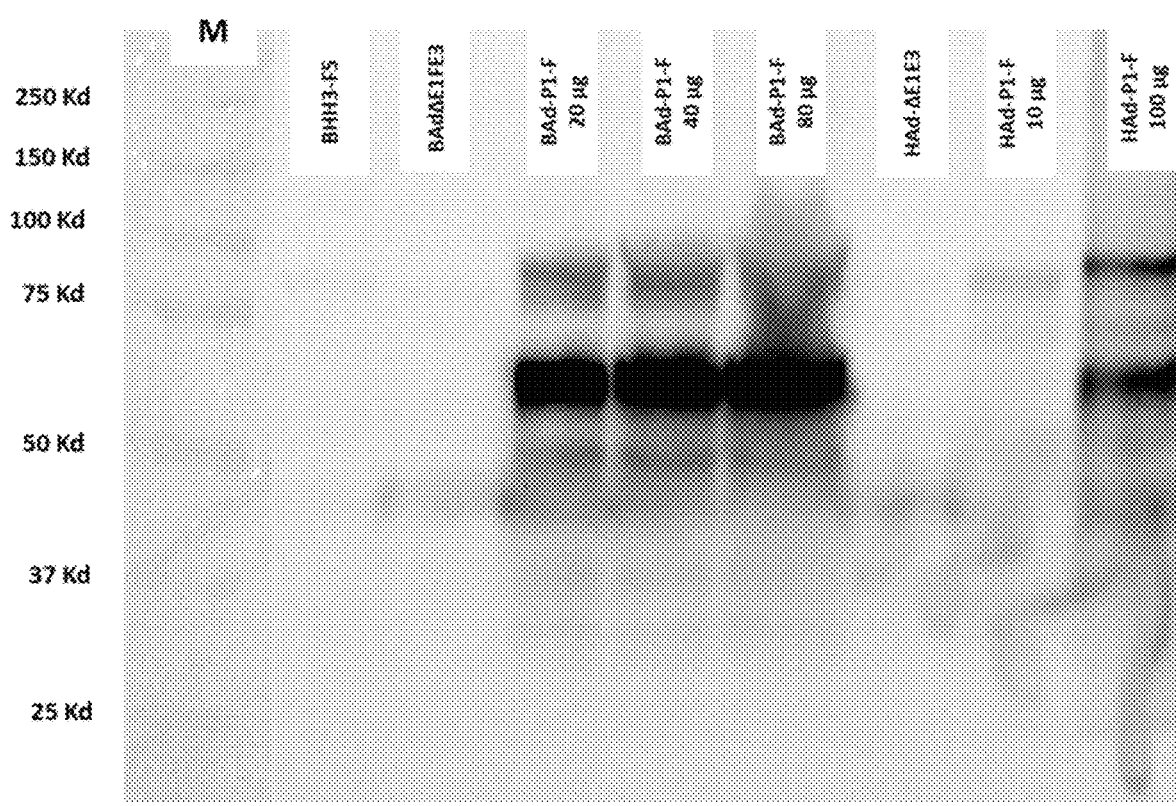

FIG. 13. Expression and processing of FMDV P1 gene construct in BAd-P1-F infected cells. BHH3-F5 [bovine human hybrid clone 3 expressing human adenovirus type 5 (HAdV-5) E1, E1B-S, E1B-L and bovine adenovirus type 3 (BAdV-3) E1B-L proteins] cells were mock (PBS) [lane: BHH3-F5] infected or infected with BAdΔE1FE3 (BAd empty vector having full E1 deletion as well as E3 deletion) or BAd-P1-F [BAdΔE1FE3 expressing foot-and-mouth disease virus (FMDV) P1 containing the furin cleavage domains, SEQ ID NO:5]. The mock or infected cells were harvested 48 h post-infection and processed for total cell protein extraction. 20, 40 or 80 μg of protein was processed for Western blot analysis. 293 cells similarly infected with HAd-ΔE1E3 (HAd empty vector having full E1 deletion as well as E3 deletion) or HAd-P1-F (HAd-ΔE1E3 expressing FMDV P1 containing the furin cleavage domains) were harvested 48 h post-infection and processed for total cell protein extraction. 10 or 100 μg of extract protein were processed for Western blot analysis. HAd-P1-F infected cell extract served as a positive control. An anti-VP2 FMDV mAb antibody (1C8B8) was used to confirm the expression and processing of P1-furin protein into VP2 and other viral proteins (VP1, VP3 and VP4). The molecular weight marker (M) are shown on the right. The dominant band at approximately 60 kDa represents the major product of P1-furin containing VP2.

FIG. 14. SEQ ID NO:4: FMDV structural proteins VP4, VP2, VP3, VP1 separated by natural sequences. The amino acids highlighted in red can be replaced by consensus furin cleavage site (RRHRR, SEQ ID NO:6).

FIG. 15. SEQ ID NO:5: Amino acid sequences of FMDV structural proteins VP4, VP2, VP3, VP1 separated by the furin cleavage site (RRHRR SEQ ID NO:6)

Figure 16:
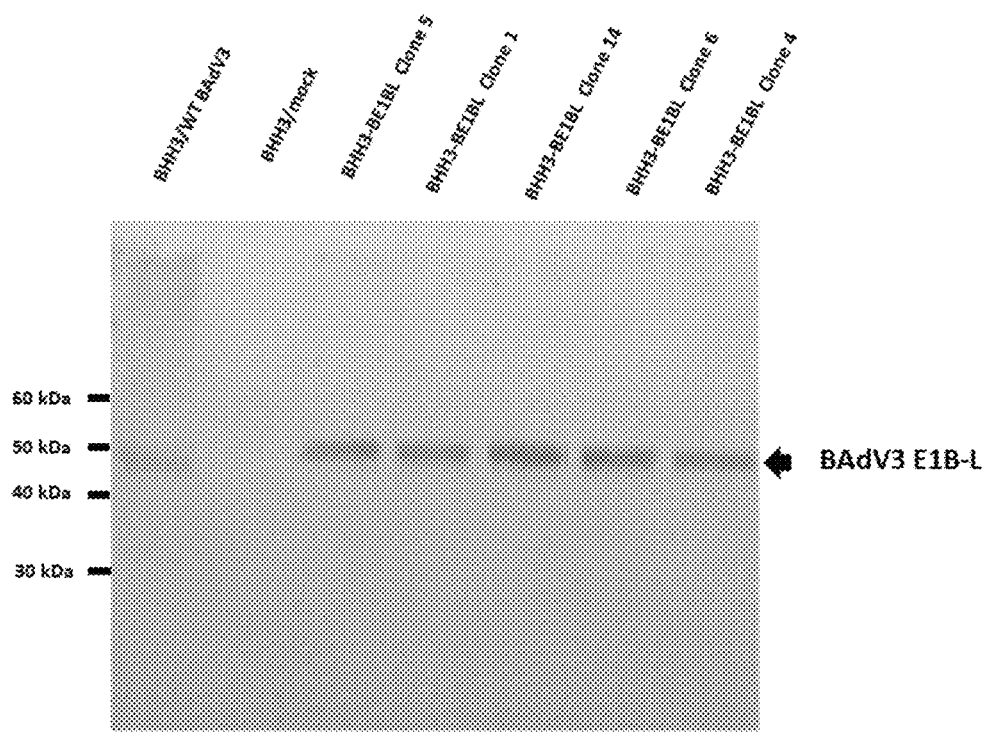

FIG. 16. Immunoblot demonstrating expression of 47 kDa BAdV-3 E1B large protein in BHH3 cell clones stably transfected with the BAdV-3 E1B large gene cassette. BHH3 cells were stably transfected with the BAdV-3 E1B large gene cassette and a number of independently generated cell clones were isolated following selection. These clones were grown as independent cell clones. Cells from a few clones (5, 1, 14, 6, and 4) were harvested and processed for western blot. Mock or wild type (WT) BAdV-3-infected cell extracts served as negative and positive control, respectively. Immunoblotting was done with a BAdV-3 E1B large protein-specific antibody raised in a rabbit. The arrow on the right side indicate the 47 kDa BAdV-3 E1B large protein band. The locations of selected molecular weight markers are indicated on the left.

FIG. 17. Replication kinetics of (A) wild type bovine adenovirus type 3 (WT BAdV-3), (B) BAdV-3 with E1A and E3 deletions (BAdV-ΔE1ΔE3), and (C) BAdV-3 with full E1A, E1B and E3 deletions (BAdV-ΔE1FE3) in MDBK, FBRT-HE1, BHH3 or BHH3-E1B/L5 (BHH3 expressing BAdV-3 E1B large protein). Cells were infected with a multiplicity of infection (m.o.i.) of 5 plaque-forming units (p.f.u.) per cell with purified WT BAdV-3, BAdV-ΔE1ΔE3 or BAdV-ΔE1ΔE3 and harvested at 6, 24, 36, 48 and 60 h post infection. Virus-infected cells along with the medium were collected and virus titration were performed by tissue culture infectious dose 50 ($TCID_{50}$) assays.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Adenovirus (AdV) vector-based vaccines have been shown to elicit a balanced humoral and cell-mediated immune (CMI) responses by activating innate immunity through both Toll-like receptor (TLR)-dependent as well as TLR-independent pathways. Due to the high prevalence of AdV in humans, the development of AdV-specific neutralizing antibodies, known as 'pre-existing vector immunity', is one of the potential concerns for several human AdV (HAdV) vector-based vaccine delivery systems. To address this concern, a number of less prevalent HAdVs or nonhuman AdVs have been developed as vaccine delivery vectors. These nonhuman AdV vectors are based on bovine AdV (BAdV), simian AdV (SAdV), porcine AdV (PAdV), ovine AdV (OAdV), Canine AdV (CAdV), avian AdV (AAdV) and murine AdV (MAdV)[8, 9].

It has been demonstrated that there were no reductions in humoral and CMI responses against the vaccine immunogen and the resultant protection efficacy of a BAdV type 3 (BAdV-3) vector-based H5N1 influenza vaccine even in the presence of exceptionally high levels of pre-existing HAdV vector immunity. In addition, pre-existing HAdV-neutralizing antibodies in humans did not cross-neutralize BAdV-3, and HAdV-specific CMI responses did not cross-react with BAdV-3. Bio-distribution, pathogenesis, transduction, and persistence studies in animal models and cell lines have suggested that the safety aspects of BAdV vectors are similar to that of HAdV vectors. It has been illustrated that the cell internalization of BAdV-3 is independent of the HAdV type C5 (HAdV-05) receptors [Coxackievirus-AdV receptor (CAR) and αvβ3 or αvβ5 integrin], but it is indicated that the α (2,3)-linked and α(2,6)-linked sialic acid receptors serve as major receptors for BAdV-3 internalization. It appears that BAdV-based vectors may serve as excellent vaccine vectors for humans without any concerns of pre-existing HAdV vector immunity.

Vaccine formulation features that are important for developing effective pre-pandemic influenza vaccine strategies include the development of a balanced humoral and CMI responses that could offer cross-protection, safety and efficacy with a single dose, dose sparing for vaccine delivery to a large number of individuals, and the capacity to produce a large number of vaccines at short notice. In our previous studies we have demonstrated that AdV vector-based vaccines could elicit potent humoral and CMI responses in mice conferring cross-protection depending on the immunogen/s of choice. Since AdV vectors have been evaluated for their efficacy as gene delivery vehicles in many clinical trials in humans, it is well understood how to produce a clinical grade of purified AdV vector lots in exceptionally large quantity under GLP conditions in certified cell lines in a short time span.

Several studies using AdV vector-based influenza vaccines have been conducted both in animal models and as clinical trials in humans to explore the potential of this vector system. Previously we have shown that Ad vector-based vaccines can provide complete protection against challenge with homologous and heterologous (antigenically distinct) influenza virus strains. Moreover, Ad vector vaccines containing multiple HA from different HA subtypes, or expressing nucleoprotein (NP) of H5N1 influenza, conferred either complete protection or significant reduction in lung virus titers, respectively, following challenge with pandemic H5, H7 or H9 influenza viruses.

The purpose of this study was to determine some of the parameters that are important for a pre-pandemic influenza vaccine including route of immunization, dose sparing, protection from a single dose, and protection against a heterologous influenza virus strain. Without being bound to any theory, the hypothesis behind this study is that a combination of HA-specific CMI responses and cross-reactive (though not necessarily cross-neutralizing) humoral immune responses will provide heterologous protection against an antigenically distinct H5N1 influenza virus. In addition, this study also focused on determining the vector type and route of immunization for enhanced immunogenicity conferring efficient protection.

In this study, we have compared the immunogenicity and efficacy of BAdV-3 vector (BAd-H5HA) expressing hemagglutinin (HA, SEQ ID NO:3) of a H5N1 influenza virus with that of HAdV-05 vector (HAd-H5HA) expressing HA of a H5N1 influenza virus in a mouse model. The vaccine doses [$1\times10^6$, $3\times10^6$, $1\times10^7$, $3\times10^7$, or $1\times10^8$ plague-forming units (PFU)] and the routes of immunization [intranasal (i.n.) or intramuscular (i.m.)] were evaluated to determine whether the BAdV vector system will serve as a better vaccine vector compared to the HAdV vector. Overall, significantly higher levels of humoral and CMI responses, and higher vaccine efficacy, in mice were observed with the BAd-H5HA vector compared to that of HAd-H5HA. The best protection efficacy, with a significantly lower vaccine dose, was observed in the mouse group inoculated i.n. with BAd-H5HA. These results suggest that the BAdV-3-based vector system is a better vaccine delivery vehicle for developing pre-pandemic influenza vaccines.

Overall, there were no significant differences in the serum anti-HA IgG, IgG1, IgG2a, and IgG2b or mucosal IgA responses in mouse groups inoculated i.m. either with BAd-H5HA or HAd-H5HA. However, mice inoculated with BAd-H5HA had higher increases in the numbers of IFNγ-secreting HA518-specific CD8 T cells in the spleen, lung and RLN than did those inoculated with HAd-H5HA. In contrast, there were no significant differences in the numbers of IFNγ-secreting HA518-specific CD8 T cells in the ILN of the mouse groups inoculated i.m. either with BAd-H5HA or HAd-H5HA. An intravenous bio-distribution study in mice has demonstrated that the BAd vector genome persists longer and with higher copy numbers in the spleen and lungs than that of the HAd vector Similar bio-distribution following the i.m. route of immunization may be responsible for the higher level of CMI responses with the BAd-H5HA vector. Additional studies will be required to determine the mechanism/s of these observations.

The HK/156 HA expressed in the AdV vectors and the HA in the challenged virus VN/1203/RG are antigenically different, so it was not surprising that the serum samples from either BAd-H5HA- or HAd-H5HA-inoculated animal groups did not have detectable levels of HI or VN titers against the challenge virus. We purposely opted for antigenically distinct HAs as an immunogen and a challenge virus to test our hypothesis that a combination of CMI responses and non-neutralizing antibodies will provide heterologous protection. The mouse group inoculated i.m. with $3\times10^7$ PFU of BAd-H5HA were completely protected from the challenge with VN/1203/RG, whereas detectable levels (0.84±0.5 log) of lung virus titers were observed in the mouse group i.m.-inoculated with $3\times10^8$ PFU of HAd-H5HA. These observations suggest that significantly higher levels of CMI responses and non-neutralizing antibodies elicited with BAd-H5HA may be responsible for enhanced protection at a significantly lower dose.

In mouse groups inoculated i.n. with BAd-H5HA, levels of serum anti-HA IgG, IgG1, IgG2a, IgG2b, mucosal anti-HA IgA, and the numbers of IFNγ-secreting HA518-specific CD8 T cells in the spleen, lung and RLN, were significantly higher than in the groups inoculated i.m. with BAd-H5HA or inoculated i.m. or i.n. with HAd-H5HA. Additional experiments are required to determine whether the high levels of humoral (systemic and mucosal) and CMI responses are due to better transduction of and/or the levels and duration of persistence of the BAd vector genomes following immunization with BAd-H5HA. Since BAd-3 utilizes the α(2,3)-linked and α(2,6)-linked sialic acid receptors as the major receptors for virus internalization, while HAd-05 uses CAR for virus entry in susceptible cells, we expect that BAd-H5HA will better transduce the respiratory tract following i.n. inoculation compared to HAd-H5HA. Moreover, the levels and duration of persistence of the BAd vector genome copy numbers in the lungs were found to be significantly higher than that of the HAd vector in an intravenous bio-distribution study. There is a possibility that a similar situation may occur following the i.n. inoculation.

Complete protection from challenge with an antigenically distinct H5N1 influenza virus VN/1203/RG was observed even in the mouse group inoculated i.n. with $1\times10^6$ PFU of BAd-H5HA, whereas similar level of protection with HAd-H5HA was only obtained with a much higher vector dose of $1\times10^8$ PFU. These observations suggest that BAd vector-based i.n. vaccine delivery system has considerable promise for dose sparing, because an approximately 100-fold lower vaccine dose of BAd-H5HA compared to HAd-H5HA conferred complete protection. Dose sparing not only lowers vaccine costs, but also increases the capacity to produce a large number of doses especially in an event similar to the influenza pandemic. Of course, additional studies will be needed to determine the long-term efficacy of cross-protective humoral and CMI responses induced by BAdV-3-based vectors.

The results described in this manuscript suggest that the BAdV-3-based vector system has many advantages over HAd systems as a vaccine delivery vehicle for developing pre-pandemic influenza vaccines. Further studies in another animal model of influenza, such as ferrets, will be essential to fully explore the potential of this vaccine delivery system. Additional studies will be required to determine the best combinational antigens or immunogenic domains that could elicit broadly cross-protective immune responses when delivered through the BAd vector system for developing a universal influenza vaccine for pandemic preparedness and to offer a better vaccine option against seasonal influenza viruses.

Material and Methods
Cell Lines, AdV Vectors, and Influenza Viruses

BHH3 (bovine-human hybrid clone 3), BHH2C (bovine-human hybrid clone 2C), 293 (human embryonic kidney cells expressing HAdV-05 E1 proteins), and MDCK (Madin-Darby canine kidney) cell lines were propagated as monolayer cultures in minimum essential medium (MEM) (Life Technologies, Gaithersburg, Md.) containing either 10% reconstituted fetal bovine serum or fetal calf serum (Hyclone, Logan, Utah) and gentamycin (50 μg/ml).

The construction and characterization of BAd-H5HA [BAdV-3 E1 and E3 deleted vector expressing HA of A/Hong Kong/156/97(H5N1) (HK/156)], BAd-ΔE1E3 (BAdV-3 E1 and E3 deleted empty vector), HAd-H5HA [HAdV-05 E1 and E3 deleted vector expressing HA of HK/156], HAd-ΔE1E3 (HAdV-05 E1 and E3 deleted empty vector), are described previously. For example, BHH3 cell lines that support the replication of BAdV vectors having only E1A deletion with or without E3 deletion are described in van Olphen AL, and Mittal SK: "Development and characterization of bovinexhuman hybrid cell lines that efficiently support the replication of both wild-type bovine and human adenoviruses and those with E1 deleted." *J Virol* 2002. 76:5882-92. FBRT-HE1 cell line (fetal bovine retinal cells which express HAdV-5 E1A, E1B-S and E1B-L proteins) is described in van Olphen AL, Tikoo SK, and Mittal SK: "Characterization of bovine adenovirus type 3 E1 proteins and isolation of E1-expressing cell lines." *Virology* 2002. 295:108-18.

BAd-H5HA and BAd-ΔE1E3 were grown and titrated in BHH3 (bovine-human hybrid clone 3 that expresses HAdV-5 E1A, E1B-S and E1B-L proteins) cells, and HAd-H5HA and HAd-ΔE1E3 were grown in 293 cells and titrated in BHH2C cells. Both BAd-H5HA and HAd-H5HA expressed HA to similar levels in vector-infected cells as observed by immunoblotting (data not shown). These vectors were purified by cesium chloride density gradient ultracentrifugation as described previously.

A/Vietnam/1203/2004(H5N1)-PR8/CDC-RG [VN/1203/RG] that was created by reverse genetics (RG) in the A/PR/8/1934(H1N1) [PR8] background was grown in embryonated hen eggs and titrated in the eggs and/or MDCK. The HA gene in the vaccine vectors was from HK/156, which is antigenically distinct from the challenge virus VN/1203/RG.

Immunogenicity and Protection Studies in Mice

All immunization and protection studies in mice were performed in a USDA-approved BSL-2+ facility with the approvals of the Institutional Animal Care and Use Committee (IACUC), and the Institutional Biosafety Committee (IBC). Six-to-eight-week-old BALB/c mice (Harlan Sprague Dawley Inc., Indianapolis, Ind.) served as the subjects for immunization and protection studies following approved guidelines.

The mouse groups (10 animals/group) were mock-inoculated (with phosphate-buffered saline (PBS), pH 7.2) or inoculated i.n. or i.m. with $1\times10^6$, $3\times10^6$, $1\times10^7$, $3\times10^7$, or $1\times10^8$ PFU of BAd-H5HA or HAd-H5HA. The mouse groups inoculated i.n. or i.m. with $1\times10^8$ PFU of BAd-ΔE1E3 or HAd-ΔE1E3 served as vector controls. Four weeks post-inoculation, 5 animals/group were anesthetized with ketamine-xylazine (90 mg/kg ketamine and 10 mg/kg xylazine) by intraperitoneal injections, the blood samples were collected via retro-orbital puncture, nasal washes were collected by washing the nasal passage with 0.5 mL of PBS, and the lung washes were prepared after homogenizing one lung from each animal in 1 mL of PBS as described previously. The serum samples, nasal washes and lung washes were used to evaluate the humoral immune responses. The second lung was processed to collect CD3+ T cells from the lung cells using MagniSort® Mouse CD3 Positive Selection Kit following the manufacturer's instructions (Affymetrix eBioscience San Diego, Calif.), and used to monitor CMI responses. The spleens, respiratory area lymph nodes (RLN) and inguinal lymph nodes (ILN) were also collected to evaluate CMI responses.

The remaining five animals per group were challenged i.n. with 100 mouse infectious dose 50 ($MID_{50}$) of VN/1203/RG. Three days post-challenge, the animals were euthanized under ketamine-xylazine anesthesia as described above, and the lungs were collected for determination of the lung virus titers as described previously.

Enzyme-Linked Immunosorbent Assay (ELISA)

ELISA was performed as described earlier. 96-well ELISA plates (eBioscience, San Diego, Calif.) were coated with purified HA protein (0.5 μg/mL) of HK/156 (MyBioSource, Inc., San Diego, Calif., USA) and incubated overnight at 4° C. Following blocking with 1% bovine serum albumin (BSA) in PBS, diluted serum samples (1:500 dilution for IgG & IgG1 and 1:50 for IgG2a and IgG2b), 1:5 diluted nasal washes, or 1:10 diluted lung washes were added and incubated at room temperature for 2 h. During the standardization process, various dilutions of each type of sample were tested to establish the best dilution. The horseradish peroxidase-conjugated goat anti-mouse IgG, IgG1, IgG2a, IgG2b, or IgA antibodies, (Invitrogenl Fisher Scientific Corp.) at a recommended dilution for each antibody was added and incubated at room temperature for 2 h. The color development was obtained with a BD OptEIA™ ELISA sets TMB substrate (Fisher Scientific Corp.). The reaction was stopped with 2N sulfuric acid solution and the optical density readings were obtained at 450 nm using a SpectraMax® i3x microplate reader (Molecular Devices, Sunnyvale, Calif.).

ELISpot Assays

The ELISpot assays were performed as described previously. The splenocytes, lung lymphocytes, RLN, and ILN were used for interferon-gamma (IFNγ) ELISpot assays after stimulating the cells with HA518 (IYSTVASSL) peptide ($H-2K^d$-restricted CTL epitope for HA). The number of spot-forming units (SFU) were counted using a dissection microscope.

Statistical Analyses

Two-way ANOVA with Bonferroni post-test were performed to determine statistical significance. The statistical significance was set at p<0.05.

EXAMPLES

Example 1. Comparison of Wild Type BAdV3 Vector Sequence Versus BAdV3ΔE1E3 Vector Sequence A map of wild type BAdV3 vector genome outline compared to BAdV3ΔE1E3 is shown in FIG. 12. As it shows, the entire E1 region of bovine adenovirus comprising 2574 nucleotides (SEQ ID NO:1) are deleted, as well as 1245 nucleotides of E3 region (SEQ ID NO:2) are also deleted. Such E1 and E3 region deleted bovine adenovirus vector increased the foreign gene cassette insertion capacity by at least 2 Kb compared to previously conventional adenovirus vector, which was not able to delete entire E1 region and still viable to produce virus in its host cell lines.

Example 2. Unique Cell Line for Producing BAdV3ΔE1E3 Viruses with or without Foreign Gene Expression The cell line used for production of empty BAd3ΔE1E3 virus or BAdV3ΔE1E3 vector with insert of HA gene is BHH3 that is also transfected with human adenovirus E1 region and bovine adenovirus type 3 EB1L gene. This cell line will support BAdV3ΔE1E3 virus replication despite the deletion of complete E1 and E3 regions in the BAdV3 vector.

In this disclosure cell lines that support the replication of BAdV vectors having E1 full deletion (including E1A, E1B-S and E1B-L) with or without E3 deletion are following:

BHH3-BE1BL (BHH3 that expresses HAdV-5 E1A, E1B-S and E1B-L proteins and BAdV-3 E1B-L protein) cell line.

BHH3-BE1B/Full (BHH3 that expresses HAdV-5 E1A, E1B-S and E1B-L proteins and BAdV-3 E1B-S and E1B-L proteins) cell line.

FBRT-HE1-BE1BL (FBRT-HE1 that expresses HAdV-5 E1A, E1B-S and E1B-L proteins and BAdV-3 E1B-L protein) cell line.

FBRT-HE1-BE1B/Full (FBRT-HE1 that expresses HAdV-5 E1A, E1B-S and E1B-L proteins and BAdV-3 E1B-S and E1B-L proteins) cell line.

In previous versions of the vectors only E1A and E3 region were deleted in BAdV-3 genome, the foreign gene cassette insertion capacity was approximately 2 Kb less compared to the E1A, E1BS and E1BL, as well as E3 region deleted vectors. However, when E1A, E1BS, E1BL of the BAdV-3 genome are deleted, the bovine cell line expressing human E1A, E1BS and E1BL cannot rescue the BAdV-3 vector, rendering foreign gene expression impossible. In the current disclosure, we transfected at least one BAdV-3 E1BL gene into a bovine cell line, together with the human E1A, human E1BS, and human E1BL genes.

Example 3

Induction of Enhanced Humoral Immune Responses with BAd-H5HA Compared to HAd-H5HA The mouse groups inoculated i.n. or i.m. once with $1\times10^6$ (FIG. 1A), $3\times10^6$ (FIG. 1B), $1\times10^7$ (FIG. 1C), $3\times10^7$ (FIG. 1D) or $1\times10^8$ (FIG. 1E) PFU of HAd-H5HA or BAd-H5HA elicited dose-dependent increases in anti-HA IgG antibody levels. These levels in the i.m.-inoculated HAd-H5HA groups were similar to or slightly better than those observed in the similarly inoculated BAd-H5HA groups. In the i.n.-inoculated BAd-H5HA groups, however, anti-HA IgG antibody levels were significantly higher than those in the similarly or i.m.-inoculated HAd-H5HA groups or the i.m.-inoculated BAd-H5HA groups. The control groups inoculated i.n. or i.m. with PBS, HAd-ΔE1E3, or BAd-ΔE1E3 did not yield anti-HA IgG antibody levels above background (FIG. 1).

We have shown previously that animals immunized with Ad vectors expressing HA produce high levels of hemagglutination inhibition (HI) and virus-neutralizing (VN) antibody titers against homologous influenza virus strains, therefore, here we only tried to determine HI and VN titers against an antigenically distinct influenza virus strain (VN/1203/RG), and noticed that none of the vaccinated groups developed any detectable HI and VN titers above the empty vector controls.

Figure 2:
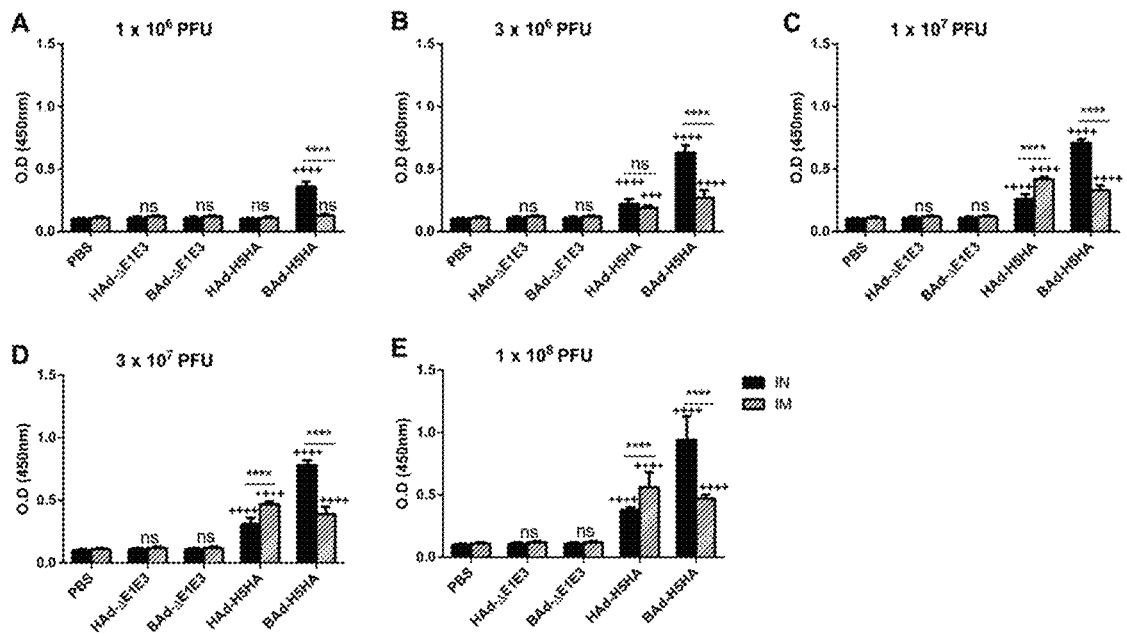
Figure 3:
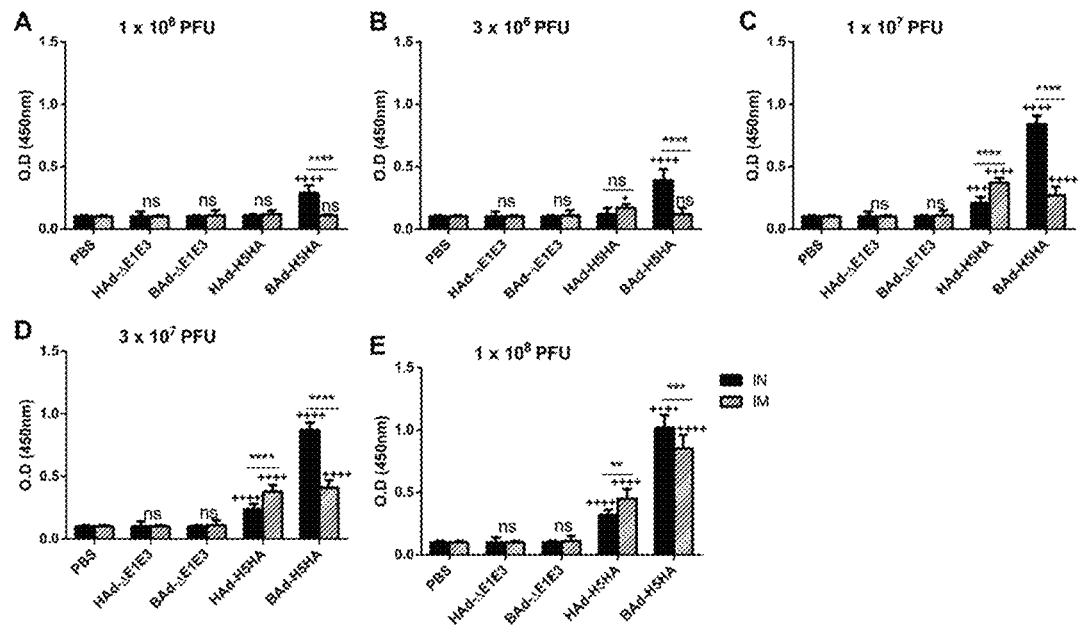
Figure 4:
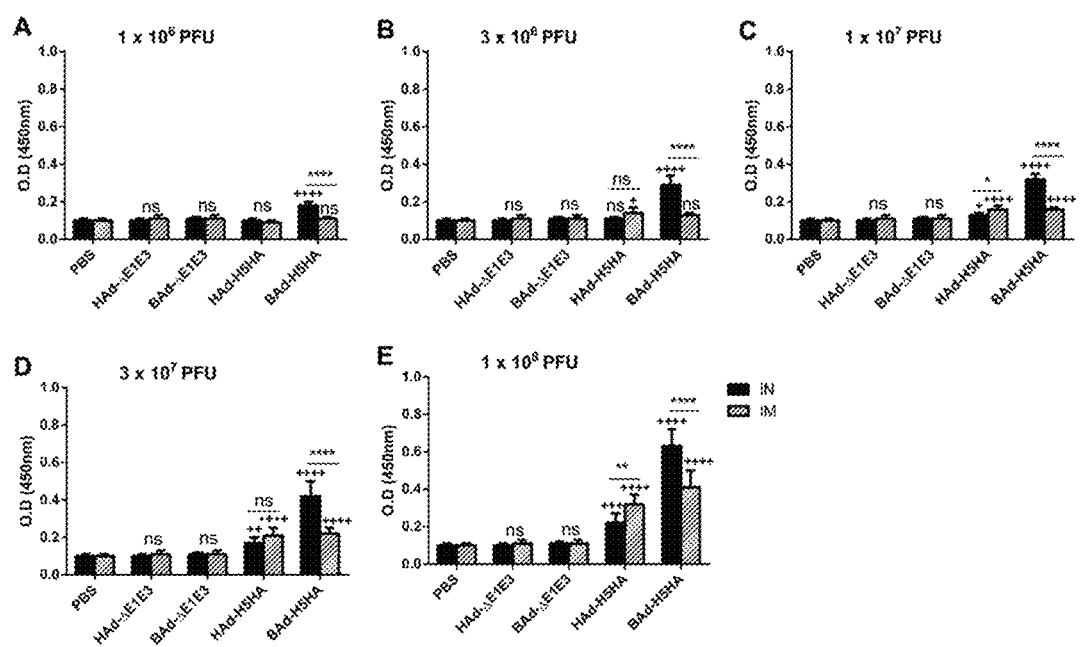

To determine whether the route of immunization or the vector type will influence the levels of IgG subclasses, the serum samples collected from the mouse groups inoculated i.n. or i.m. once with $1\times10^6$ (FIGS. 2A, 3A & 4A), $3\times10^6$ (FIGS. 2B, 3B & 4B), $1\times10^7$ (FIGS. 2C, 3C & 4C), $3\times10^7$ (FIGS. 2D, 3D & 4D) or $1\times10^8$ (FIGS. 2E, 3E & 4E) PFU of HAd-H5HA or BAd-H5HA were analyzed for anti-HA IgG1 (FIG. 2), IgG2a (FIG. 3) and IgG2b (FIG. 4) levels by ELISA, respectively. As expected, there were dose-dependent increases in anti-HA IgG1, IgG2a and IgG2b antibody levels. These levels in the i.m.-inoculated HAd-H5HA groups were similar to or slightly better or lower than those observed in the i.m.-inoculated BAd-H5HA groups. However, in the i.n.-inoculated BAd-H5HA groups, anti-HA IgG1, IgG2a and IgG2b antibody levels were significantly higher than those in the i.n.- or i.m.-inoculated HAd-H5HA groups or the i.m.-inoculated BAd-H5HA groups (FIGS. 2, 3 & 4). Control groups inoculated i.n. or i.m. with PBS, HAd-ΔE1E3, or BAd-ΔE1E3 did not yield anti-HA IgG1 (FIG. 2), IgG2a (FIG. 3) or IgG2b (FIG. 4) antibody levels above background.

Furthermore, to ascertain if the route of immunization or the vector type will influence the development of HA-specific IgA responses at the mucosal level, lung washes (FIG. 5) as well as nasal washes (FIG. 6) from the mouse groups inoculated i.n. or i.m. once with $1\times10^6$ (FIGS. 5A & 6A), $3\times10^6$ (FIGS. 5B & 6B), $1\times10^7$ (FIGS. 5C & 6C), $3\times10^7$ (FIGS. 5D & 6D) or $1\times10^8$ (FIGS. 5E & 6E) PFU of HAd-H5HA or BAd-H5HA were analyzed for anti-HA IgA levels by ELISA. As expected, there were dose-dependent increases in anti-HA IgA antibody levels in the lung washes as well as nasal washes. IgA antibody levels in the lung washes and nasal washes in the i.m.-inoculated BAd-H5HA or HAd-H5HA groups were detected only with doses of $1\times10^7$ PFU and onwards (FIGS. 5 & 6). IgA antibody levels in the lung washes and nasal washes of the i.m.-inoculated BAd-H5HA groups were similar to or slightly higher than those in the i.m.-inoculated HAd-H5HA, whereas IgA antibody levels in the lung washes and nasal washes in the i.n.-inoculated BAd-H5HA or HAd-H5HA groups were detected with the lowest dose of $1\times10^6$ PFU and onwards. In the i.n.-inoculated BAd-H5HA groups, anti-HA IgA antibody levels in the lung washes (FIG. 5) and nasal washes (FIG. 6) were significantly higher than those in the i.n.- or i.m.-inoculated HAd-H5HA groups or the i.m.-inoculated BAd-H5HA groups. The control groups inoculated i.n. or i.m. with PBS, HAd-ΔE1E3, or BAd-ΔE1E3 did not yield anti-HA IgA antibody levels above background (FIGS. 5 & 6).

Example 4

Induction of Enhanced CMI Responses with BAd-H5HA Compared to HAd-H5HA

CMI responses against influenza viruses are important for virus clearance following infection and play an important role in heterologous as well as heterosubtypic protection against influenza viruses. To verify whether the route of immunization or the vector type will impact the development of the CMI responses against influenza in vaccinated mice, we analyzed splenocytes (FIG. 7), pooled RLN cells (FIG. 8), pooled ILN cells (FIG. 9), and pooled lung lymphocytes (FIG. 10) from AdV vector-inoculated groups for HA-specific CMI responses following in vitro stimulation with HA518 using an IFNγ-specific ELISpot assay. The numbers of IFNγ-secreting HA518-specific CD8 T cells from the mouse groups inoculated i.n. or i.m. once with $1\times10^6$ (FIGS. 7A, 8A, 9A & 10A), $3\times10^6$ (FIGS. 7B, 8B, 9B & 10B), $1\times10^7$ (FIGS. 7C, 8C, 9C & 10C), $3\times10^7$ (FIGS. 7D, 8D, 9D & 10D) or $1\times10^8$ (FIGS. 7E, 8E, 9E & 10E) PFU of HAd-H5HA or BAd-H5HA are shown. There were dose-dependent increases in the numbers of IFNγ-secreting HA518-specific CD8 T cells in splenocytes (FIG. 7), pooled RLN cells (FIG. 8), pooled SLN cells (FIG. 9), and pooled lung lymphocytes (FIG. 10) of the vaccinated groups compared with the empty vector (Ad-ΔE1E3) or PBS control groups. There were significantly higher numbers of IFNγ-secreting HA518-specific CD8 T cells in splenocytes of the i.m.- or i.n.-inoculated BAd-H5HA groups compared to the i.m.- or i.n.-inoculated HAd-H5HA groups (FIG. 7), and the numbers were consistently higher in the i.m.-inoculated vaccine groups compared to that of the i.n. inoculated vaccine groups.

There were substantially higher numbers of IFNγ-secreting HA518-specific CD8 T cells in the RLN of the i.m.- or i.n.-inoculated BAd-H5HA groups compared to those of the i.m.- or i.n.-inoculated HAd-H5HA groups (FIG. 8), and the numbers were consistently higher in the i.n.-inoculated vaccine groups compared to those of the i.m.-inoculated vaccine groups. Whereas in ILN of the i.m.-inoculated vaccine groups, higher numbers of IFNγ-secreting HA518-specific CD8 T cells were detected compared to those of the empty vector (Ad-ΔE1E3) or PBS control groups or the i.n.-inoculated vaccine groups (FIG. 9), and the numbers were consistently higher in the i.m.-inoculated vaccine groups compared to those of the i.n.-inoculated vaccine groups. Furthermore, considerably elevated numbers of IFNγ-secreting HA518-specific CD8 T cells in the lung lymphocytes of the i.m.- or i.n. inoculated BAd-H5HA groups compared to those of the i.m.- or i.n.-inoculated HAd-H5HA groups, respectively, were visualized (FIG. 10), and the numbers were consistently higher in the i.n.-inoculated vaccine groups compared to those of the i.m.-inoculated vaccine groups.

Example 5

Development of Enhanced Protection in Mice Immunized with BAd-H5HA Compared to HAd-H5HA Since the influenza virus VN/1203/RG, which was used as a challenge virus to evaluate the efficacy of protection, does not cause significant morbidity or mortality in mice, significant reductions in lung viral titers in vaccinated animals following challenge is a useful measure of the virus clearance and vaccine protective efficacy. The mouse groups were immunized i.n. or i.m. once with $1\times10^6$ (FIG. 11A), $3\times10^6$ (FIG. 11B), $1\times10^7$ (FIG. 11C), $3\times10^7$ (FIG. 11D) or $1\times10^8$ (FIG. 11E) PFU of HAd-H5HA or BAd-H5HA, and subsequently challenged with 100 MID$_{50}$ of VN/1203/RG. For the i.n. route of inoculation, the lowest vaccine dose of $1\times10^6$ PFU of BAd-H5HA conferred complete protection following challenge (FIG. 11A). The lowest vaccine dose for i.n.-inoculated HAd-H5HA that yielded complete protection following challenge was $3\times10^7$ PFU (FIG. 11E). For the i.m. route of inoculation, the lowest vaccine dose for BAd-H5HA that conferred complete protection following challenge was $3\times10^7$ PFU (FIG. 11D). For the i.m.-inoculated HAd-H5HA animal group, the log lung virus titer with a dose of $1\times10^8$ PFU was 1.84±1.14, compared to 4.90±0.42 and 4.6±0.46 log lung virus titers in the empty vector (HAd-ΔE1E3) or PBS control groups, respectively (FIG. 11E). Even at a challenge dose of $3\times10^8$ PFU per animal for i.m.-inoculated HAd-H5HA animal group, log lung virus titers of 0.84±0.5 was observed.

Example 6. Expression and Processing of FMDV P1 Gene Construct in BAd-P1-F Infected Cells This is another example of a BAdV-3 vector with full E1 region and E3 region deletion with a foreign gene cassette in the E1 deleted region to express a target antigen in a bovine cell line that complement E1 gene functions. In this example, foot and mouse disease virus (FMDV) P1 gene is inserted to BAdV-3ΔE1E3, and the resulted vector construct is transfected into bovine human hybrid clone 3 expressing human adenovirus type 5 (HAdV-5) E1, E1B-S, E1B-L and bovine adenovirus type 3 (BAdV-3) E1B-L proteins. Successful detection of the P1 gene and its processed structural proteins are shown in FIG. 13. The cells were mock (PBS) [lane: BHH3-F5] infected or infected with BAdΔE1FE3 (BAd empty vector having full E1 deletion as well as E3 deletion) or BAd-P1-F [BAdΔE1FE3 expressing foot-and-mouth disease virus (FMDV) P1 containing the furin cleavage domains]. The mock or infected cells were harvested 48 h post-infection and processed for total cell protein extraction. 20, 40 or 80 μg of protein was processed for Western blot analysis. 293 cells similarly infected with HAd-ΔE1E3 (HAd empty vector having full E1 deletion as well as E3 deletion) or HAd-P1-F (HAd-ΔE1E3 expressing FMDV P1 containing the furin cleavage domains) were harvested 48 h post-infection and processed for total cell protein extraction. 10 or 100 μg of extract protein were processed for Western blot analysis. HAd-P1-F infected cell extract served as a positive control. An anti-VP2 FMDV mAb antibody (1C8B8) was used to confirm the expression and processing of P1-furin protein into VP2 and other viral proteins (VP1, VP3 and VP4). The molecular weight marker (M) are shown on the right. The dominant band at approximately 60 kDa represents the major product of P1-furin containing VP2.

Example 7. Generation of a Cell Line Expressing E1 Proteins (E1A, E1B Small and E1B Large) of Human AdV Type C5 (HAdV-05) and the E1B Large Protein of BAdV-3

Our repeated efforts to generate BAdV-3 vectors with a full deletion in E1 region using cell lines expressing HAdV-05 E1 proteins (BHH3 or FBRT-HE1) were unsuccessful, whereas we could generate BAdV vectors having deletion of E1A in these cell lines. These observations suggested that either both E1B proteins (small and large) or at least E1B large protein function/s is/are not complemented for BAdV-3 E1B protein/s. Using BHH3 or FBRT-HE1 cell line, we generated stable clones expressing BAdV-3 E1B proteins (small and large) or expressing BAdV-3 E1B large. BHH3 cell clones expressing 47 kDa BAdV-3 E1B large protein as demonstrated by immunoblotting is shown (FIG. 16). On the basis of cell growth and expression characteristics, BHH3-BE1B/L5 was selected for further use.

Example 8. Growth Kinetics of WT BAdV-3, BAdV-ΔE1ΔE3 (BAdV-3 with E1A and E3 Deletions), and BAdV-ΔE1FE3 (BAdV-3 with Full E1A, E1B and E3 Deletions)

Figure 17:
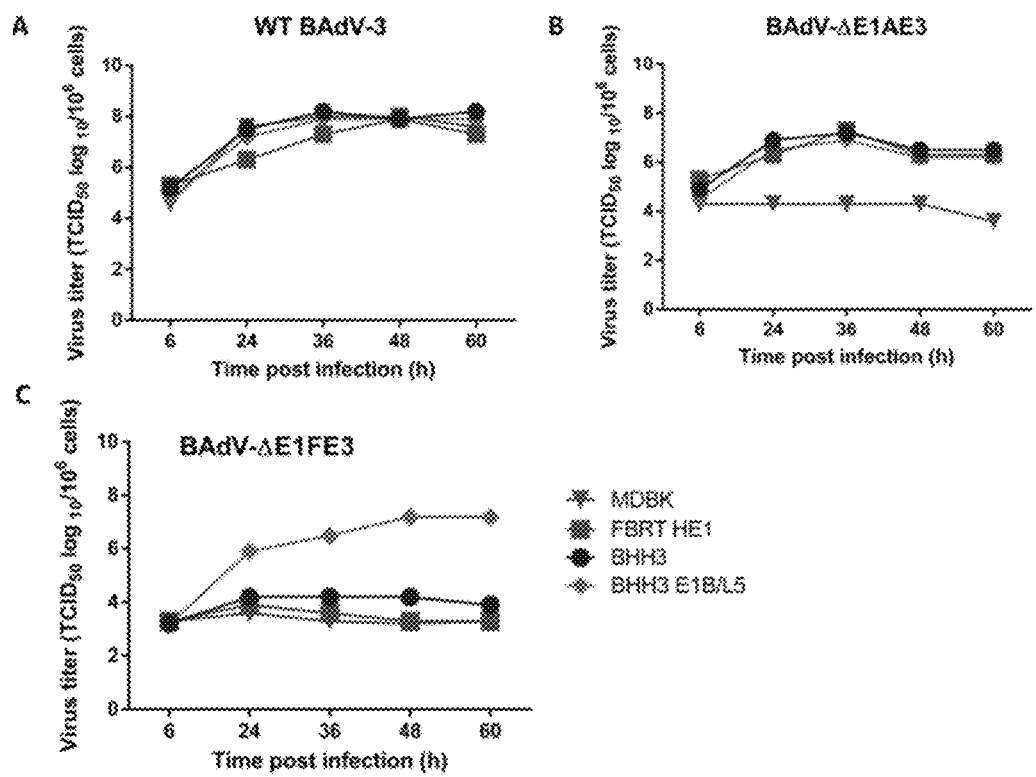

Growth kinetics of WT BAdV-3, BAdV-ΔE1ΔE3, and BAdV-ΔE1FE3 were performed in MDBK, FBRT-HE1 (expressing HAdV-05 E1 proteins), BHH3 (expressing HAdV-05 E1 proteins) or BHH3-E1B/L5 (BHH3 expressing BAdV-3 E1B large protein). The purpose was to determine whether expression of BAdV-3 E1B large protein is essential for the replication of BAdV-ΔE1FE3 (having 2574 bps E1 deletion and 1245 bps E3 deletion). WT BAdV-3 replicated equally well in all cell lines (FIG. 17A) since its replication does not require any complementation of E1 functions. Since BAdV-ΔE1ΔE3 requires the complementation of E1A function, it replicated to similar titers in E1A complementing cell lines (BHH3, FBRT-HE1 and BHH3-E1B/L5) (FIG. 17B). Whereas, BAdV-ΔE1FE3 replicated only in BHH3-E1B/L5 cells (FIG. 17C) indicating that BAdV-3 vectors with full E1 deletion requires the complementation of F1B large function from the BAdV-3 E1B large protein.

The invention claimed is:

1. A vaccine production system comprising a bovine cell line co-transfected with
   a. human adenovirus (HAdV) E1 region;
   b. a bovine adenovirus E1BL gene; and
   c. a bovine adenovirus type 3 (BAdV3) vector with E1A, E1BS, E1BL and E3 regions replaced by an antigenic gene.

2. The vaccine production system of claim 1, wherein the antigenic gene is hemagglutinin (HA) of an influenza virus.

3. The vaccine production system of claim 1, wherein the antigenic gene is the P1 gene or its constituents VP1, VP2, VP3, VP4, or a combination thereof, of Foot and Mouth Disease virus.

4. The bovine adenovirus type 3 (BAdV3) vector with E1A, E1BS, E1BL and E3 regions deleted and a foreign gene up to 5.5kb inserted for expression under the control of an effective promoter at the site of deletion, wherein the foreign gene comprises SEQ ID NO: 8.

5. The vaccine production system according to claim 1, wherein the antigenic gene expresses a protein sequence selected from the group consisting of SEQ ID NOs: 3, 4, 5 and 9.

* * * * *